(12) United States Patent
Lee et al.

(10) Patent No.: US 10,219,784 B2
(45) Date of Patent: Mar. 5, 2019

(54) METHOD OF VARIABLE EDITING ULTRASOUND IMAGES AND ULTRASOUND SYSTEM PERFORMING THE SAME

(71) Applicant: SAMSUNG MEDISON CO., LTD., Hongcheon-gun (KR)

(72) Inventors: Kwang-hee Lee, Hongcheon-gun (KR); Jun-sang Yoo, Hongcheon-gun (KR)

(73) Assignee: SAMSUNG MEDISON CO., LTD., Hongcheon-gun (KR)

(*) Notice: Subject to any disclaimer, the term of this patent is extended or adjusted under 35 U.S.C. 154(b) by 738 days.

(21) Appl. No.: 14/696,613

(22) Filed: Apr. 27, 2015

(65) Prior Publication Data
US 2016/0058418 A1 Mar. 3, 2016

(30) Foreign Application Priority Data

Sep. 2, 2014 (KR) .................. 10-2014-0116370

(51) Int. Cl.
*G06F 3/048* (2013.01)
*A61B 8/00* (2006.01)
(Continued)

(52) U.S. Cl.
CPC ............. *A61B 8/468* (2013.01); *A61B 8/08* (2013.01); *A61B 8/463* (2013.01); *A61B 8/465* (2013.01); *A61B 8/467* (2013.01); *A61B 8/5223* (2013.01); *A61B 8/54* (2013.01); *G06F 3/04845* (2013.01); *A61B 8/12* (2013.01)

(58) Field of Classification Search
CPC ............. A61B 8/14; A61B 8/54; G16H 30/40
See application file for complete search history.

(56) References Cited

U.S. PATENT DOCUMENTS

2007/0110291 A1  5/2007  Ahn et al.
2008/0208047 A1* 8/2008  Delso ............... A61B 8/00
                                                    600/437
(Continued)

FOREIGN PATENT DOCUMENTS

JP   2005-87591 A    4/2005
KR   100978476 B1    8/2010
(Continued)

OTHER PUBLICATIONS

Saini, K., Dewal, M. L., Rohit, M., "Ultrasound Imaging and Image Segmentation in the area of Ultrasound: A Review", International Journal of Advanced Science and Technology, vol. 24, Nov. 2010, Sections 2.2.1, 2.2.2, 3.5, pp. 42-44 and 49-50.*

(Continued)

*Primary Examiner* — Claudia Dragoescu
(74) *Attorney, Agent, or Firm* — Sughrue Mion, PLLC

(57) ABSTRACT

An ultrasound system and a method of editing a label displayed with an ultrasound image are provided. The ultrasound system displays a plurality of labels generated based on a predetermined threshold value on the ultrasound image, receives a selection signal for selecting at least one label from the plurality of labels and an adjustment signal for adjusting the predetermined threshold value, generates at least one new label based on a threshold value adjusted according to the adjustment signal, and replaces and displays some of the at least one new label on a region corresponding to the at least one selected label.

25 Claims, 16 Drawing Sheets

(51) Int. Cl.
A61B 8/08 (2006.01)
G06F 3/0484 (2013.01)
A61B 8/12 (2006.01)

(56) References Cited

U.S. PATENT DOCUMENTS

| | | | |
|---|---|---|---|
| 2008/0267499 A1* | 10/2008 | Deischinger | G06K 9/3233 382/173 |
| 2009/0192386 A1 | 7/2009 | Hashimoto | |
| 2011/0087095 A1 | 4/2011 | Lee | |
| 2011/0119609 A1* | 5/2011 | Bhatt | G06F 3/0481 715/765 |
| 2012/0207360 A1* | 8/2012 | Mehanian | G06K 9/0014 382/128 |
| 2013/0165789 A1 | 6/2013 | Yao et al. | |
| 2016/0012585 A1 | 1/2016 | Lee | |

FOREIGN PATENT DOCUMENTS

| | | | |
|---|---|---|---|
| KR | 1020110039932 A | 4/2011 | |
| KR | 10-1100457 B1 | 12/2011 | |
| KR | 10-1107487 B1 | 1/2012 | |
| KR | 10-1124153 B1 | 3/2012 | |
| KR | 1020130090740 A | 8/2013 | |

OTHER PUBLICATIONS

Communication dated May 31, 2016, issued by the Korean Intellectual Property Office in counterpart Korean Application No. 10-2014-0116370.

Communication dated Oct. 29, 2015 issued by the Korean Intellectual Property Office in counterpart Application No. 10-2014-0116370.

Raine-Fenning, et al., "SonoAVC: a novel method of automatic volume calculation", Ultrasound in Obstetrics and Gynecology, vol. 31, Issue No. 6, pp. 691-696, Jan. 1, 2008, XP 055247949, http://dx.doi.org/10.1002/uog.5359.

Noble, et al., "Ultrasound Image Segmentation: A Survey", IEEE Transactions on Medical Imaging, vol. 25, Issue No. 8, pp. 987-1010, Aug. 1, 2006, XP 008085509, http://dx.doi.org/10.1109/TMI.2006.877092.

Vandekerckhove, et al. "The value of automated follicle volume measurements in IVF/ICSI" Frontiers in Surgery, vol. 90, Suppl. Issue No. 1, May 28, 2014, pp. 1-12, XP 0055247948, http://dx.doi.org/10.1016/j.fertnstert.2009.02.058.

Rodriguez-Fuentes, et al., "Prospective evaluation of automated follicle monitoring in 58 in vitro fertilization cycles: follicular volume as a new indicator of oocyte maturity", Fertility and Sterility, vol. 93, Issue No. 2, Jan. 15, 2010, pp. 616-620, http://dx.doi.org/10.1016/j.fertnstert.2009.02.058 (URL link listed provided with fourth listed document in "Documents cited:" section on p. 2 of Cite No. 7 ("Extract from the Register of European Patents")).

Communication dated Feb. 16, 2016, issued by the European Patent Office in counterpart European Patent Application No. 15157869.7.

Communication dated Mar. 16, 2016, issued by the European Patent Office in counterpart European Patent Application No. 15157869.7, "Extract from the Register of European Patents".

Communication dated May 20, 2016, issued by the European Patent Office in counterpart European Patent Application No. 15157869.7.

* cited by examiner

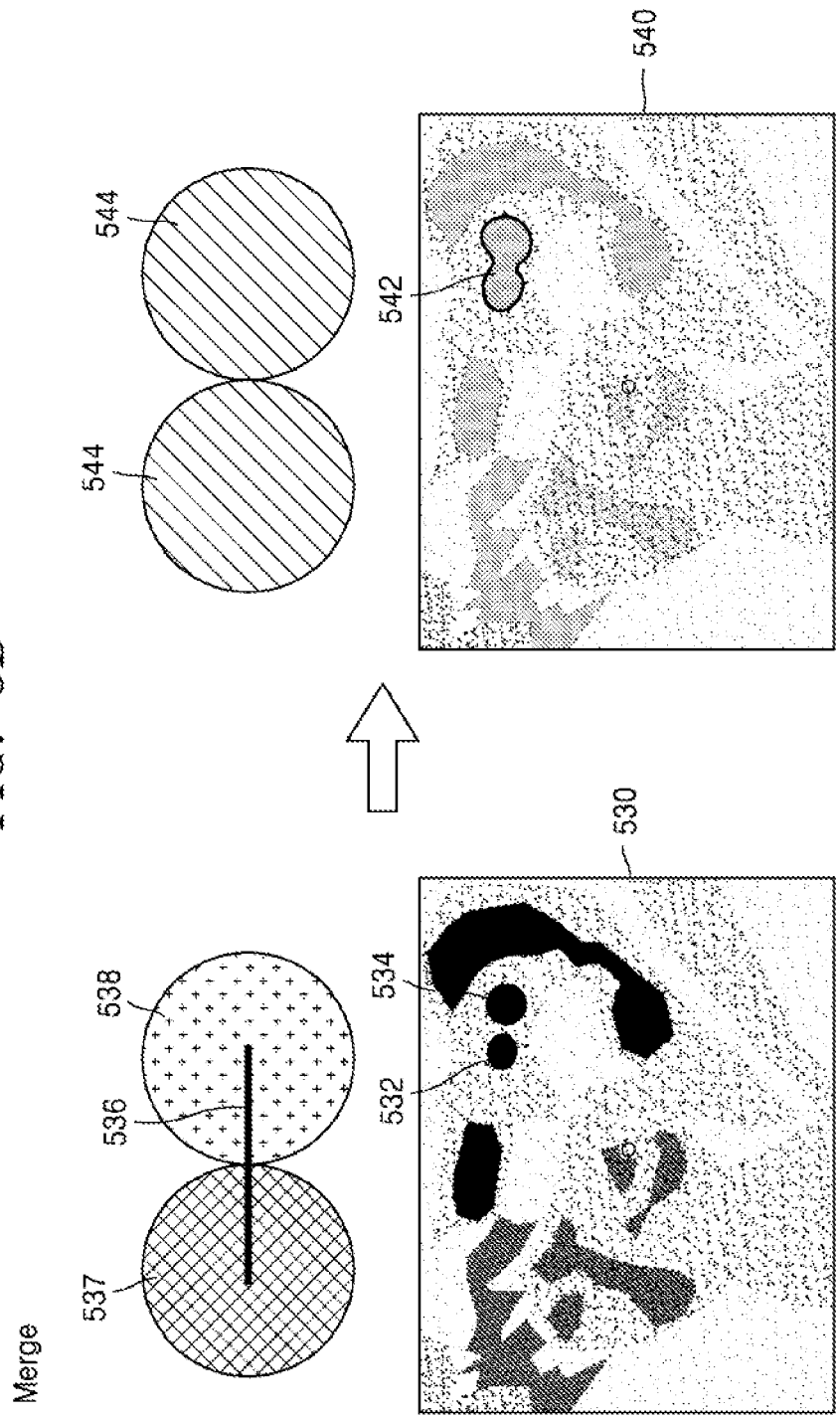

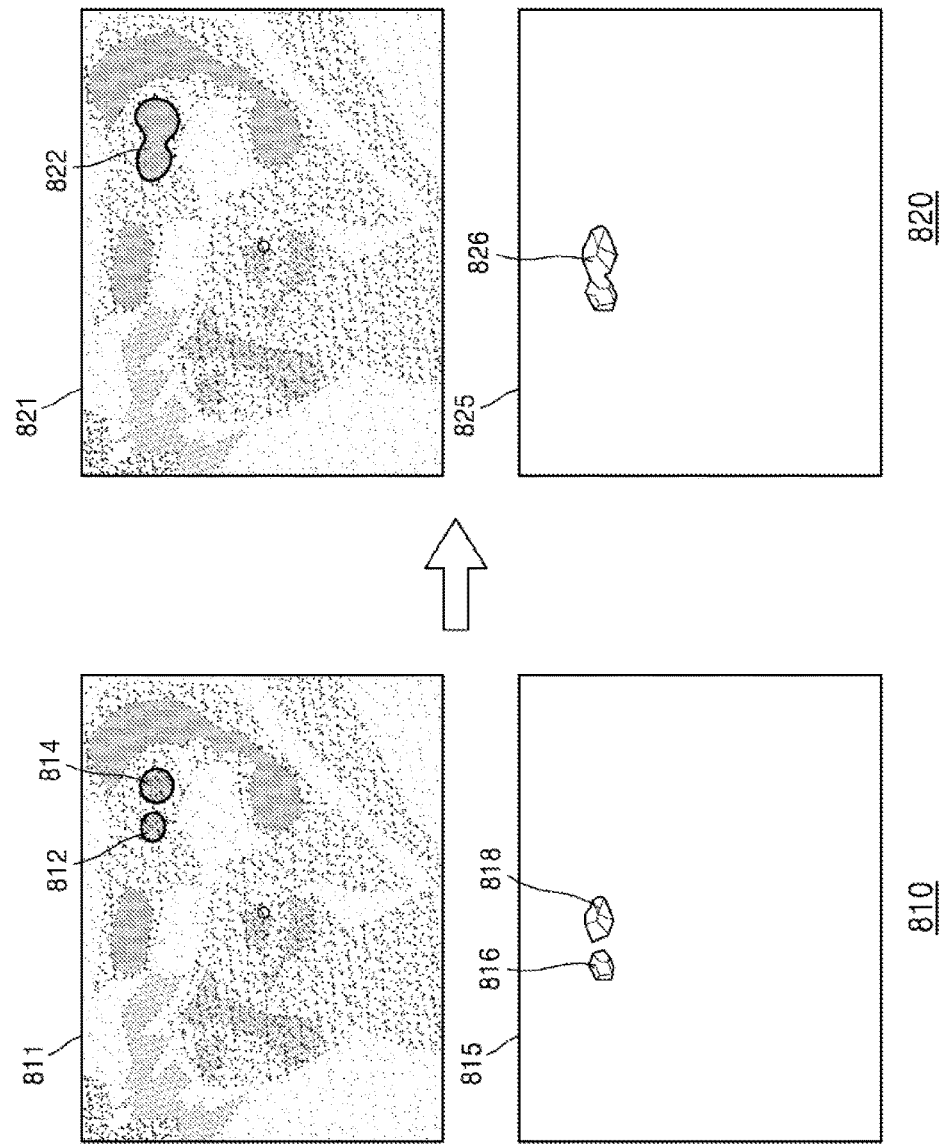

METHOD OF VARIABLE EDITING ULTRASOUND IMAGES AND ULTRASOUND SYSTEM PERFORMING THE SAME

RELATED APPLICATION

This application claims the benefit of Korean Patent Application No. 10-2014-0116370, filed on Sep. 2, 2014, in the Korean Intellectual Property Office, the disclosure of which is incorporated herein in its entirety by reference.

BACKGROUND

1. Field

One or more exemplary embodiments relate to a method of editing ultrasound images and an ultrasound system performing the method, and more particularly, to a variable editing method regarding geometric shapes of regions displayed on ultrasound images and an ultrasound system performing the method.

2. Description of the Related Art

Ultrasound diagnosis apparatuses transmit ultrasound signals generated by transducers of a probe to an object and receive information of echo signals reflected from the object, thereby obtaining at least one image of an internal part of the object. In particular, the ultrasound diagnosis apparatuses are used for medical purposes including observation of the interior of an object, detection of foreign substances, and diagnosis of damage to the object. Compared to X-ray apparatuses, such ultrasound diagnosis apparatuses provide high stability, display images in real time, and are safe due to lack of radioactive exposure. Therefore, ultrasound diagnosis apparatuses are widely used together with other image diagnosis apparatuses.

The ovary in a female body has a plurality of follicles. According to an ovulation period, one of the follicles may increase in size and be released from the ovary (ovulation). However, if the follicle fails to release from the ovary and remains inside, cysts may be generated. The non-occurrence of ovulation may cause an irregular menstrual cycle and sterility.

FIG. 1 is a view of a normal ovary 110 and a polycystic ovary 120. Referring to FIG. 1, a follicle 112 among a plurality of follicles in the normal ovary 110 may increase in size and be released from the ovary. Follicles that were not released normally may remain in the polycystic ovary 120 and transform into cysts 122.

Polycystic ovary syndrome may be diagnosed when at least five small cysts, each having a diameter of less than 10 mm and formed in a shape of a pearl necklace, are observed on a cross-section of the ovary by performing ultrasound diagnosis. In general, cysts are darker than the ovary in an ultrasound image. Korean Patent Application No. 10-2009-0097003 (US 2011/0087095 A1) discloses technology for conveniently and accurately extracting cysts by detecting certain regions based on the brightness of an ultrasound image and automatically distinguishing the regions by using labels.

However, since some labels that are automatically generated by an ultrasound system may not be accurate, a method of accurately and conveniently editing automatically generated labels is necessary.

SUMMARY

According to one or more exemplary embodiments, an ultrasound system includes a display displaying an ultrasound image generated based on ultrasound volume data obtained from an object and a plurality of labels generated based on the ultrasound volume data and a predetermined threshold value; a user interface receiving a selection signal for selecting at least one label from the plurality of labels and an adjustment signal for adjusting the predetermined threshold value; and a controller generating at least one new label based on a threshold value adjusted according to the adjustment signal. The display replaces and displays the at least one new label on a region corresponding to the at least one selected label.

When the display replaces and displays the at least one new label in a region which corresponds to the at least one selected label, at least one label that is not selected according to the selection signal from among the plurality of labels generated based on the predetermined threshold value may be displayed as it is.

The ultrasound volume data may include a plurality of voxels, and the selection signal may be for selecting coordinate information corresponding to at least one voxel included in the at least one selected label.

The selection signal may be for inputting a straight line or a curved line crossing at least two labels selected from the plurality of labels or for inputting coordinate information in regions corresponding to the at least two labels.

When a first label is selected from the plurality of labels according to the selection signal, the display may display a second label on a region corresponding to the first label based on the adjusted threshold value. The second label may be larger or smaller than the first label.

When the ultrasound volume data includes a plurality of voxels and the plurality of labels include a first label, the number of voxels included in the first label according to the predetermined threshold value may be different from the number of voxels included in the second label according to the adjusted threshold value.

When a first label is selected from the plurality of labels according to the selection signal, the display may separately display at least two labels based on the adjusted threshold value on a region corresponding to the first label.

When a first label is selected from the plurality of labels according to the selection signal and a threshold value used to generate the at least one new label is gradually changed from the predetermined threshold value to the adjusted threshold value according to the adjustment signal, a label displayed on a region corresponding to the first label may be gradually reduced in size and then split into at least two labels.

When a first label and a second label are selected from the plurality of labels according to the selection signal, the display may display a third label, which indicates that the first and second labels are merged based on the adjusted threshold value, on a combined region corresponding to the first and second labels.

When a first label and a second label are selected from the plurality of labels according to the selection signal and a threshold value used to generate the at least one new label is gradually changed from the predetermined threshold value to the adjusted threshold value according to the adjustment signal, a label displayed on a region corresponding to the first label and a label displayed on a region corresponding to the second label may be respectively gradually increased in size and merged into a third label.

The ultrasound volume data may include a plurality of voxels. When the user interface receives a selection input for selecting coordinates corresponding to a voxel not included in the plurality of labels according to the selection signal, the display may display at least one new label generated based on the adjusted threshold value on a region including the coordinates.

When a first label is selected from the plurality of labels, the display may not display any labels based on the adjusted threshold value on a region corresponding to the first label.

When a first label is selected from the plurality of labels according to the selection signal and a threshold value used to generate the at least one new label is gradually changed from the predetermined threshold value to the adjusted threshold value according to the adjustment signal, a label displayed on a region corresponding to the first label may be gradually reduced in size and deleted.

According to one or more exemplary embodiments, a method of displaying a label in an ultrasound system includes displaying an ultrasound image generated based on ultrasound volume data obtained from an object and a plurality of labels generated based on the ultrasound volume data and a predetermined threshold value; receiving a selection signal for selecting at least one label from the plurality of labels; receiving an adjustment signal for adjusting the predetermined threshold value; generating at least one new label based on a threshold value adjusted according to the adjustment signal; replacing and displaying the at least one new label on a region corresponding to the at least one selected label.

BRIEF DESCRIPTION OF THE DRAWINGS

These and/or other aspects will become apparent and more readily appreciated from the following description of the exemplary embodiments, taken in conjunction with the accompanying drawings. Reference numerals indicate structural elements.

FIGS. 5A and 5B are schematic views of a method of splitting or merging labels generated in ultrasound images;

FIGS. 8A to 8D are views of processes of splitting, merging, or deleting a generated label or newly generating a label according to an input of a user, according to an embodiment;

DETAILED DESCRIPTION

The terms used in this specification are those general terms currently widely used in the art in consideration of functions regarding the present inventive concept, but the terms may vary according to the intention of those of ordinary skill in the art, precedents, or new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

Throughout the specification, it will also be understood that when a component "includes" an element, unless there is another opposite description thereto, it should be understood that the component does not exclude another element and may further include another element. In addition, terms such as ". . . unit," ". . . module," or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Furthermore, the object may be a phantom. The phantom means a material having a density, an effective atomic number, and a volume that are approximately the same as those of an organism. For example, the phantom may be a spherical phantom having properties similar to a human body.

Furthermore, throughout the specification, a "user" may be, but is not limited to, a medical expert, such as a medical doctor, a nurse, a medical laboratory technologist, a medical image expert, or a technician who repairs a medical apparatus.

Exemplary embodiments will now be described more fully hereinafter with reference to the accompanying drawings, in which illustrative exemplary embodiments of the inventive concept are shown. As used herein, the term "and/or" includes any and all combinations of one or more of the associated listed items. Expressions such as "at least one of," when preceding a list of elements, modify the entire list of elements and do not modify the individual elements of the list.

Figure 1:
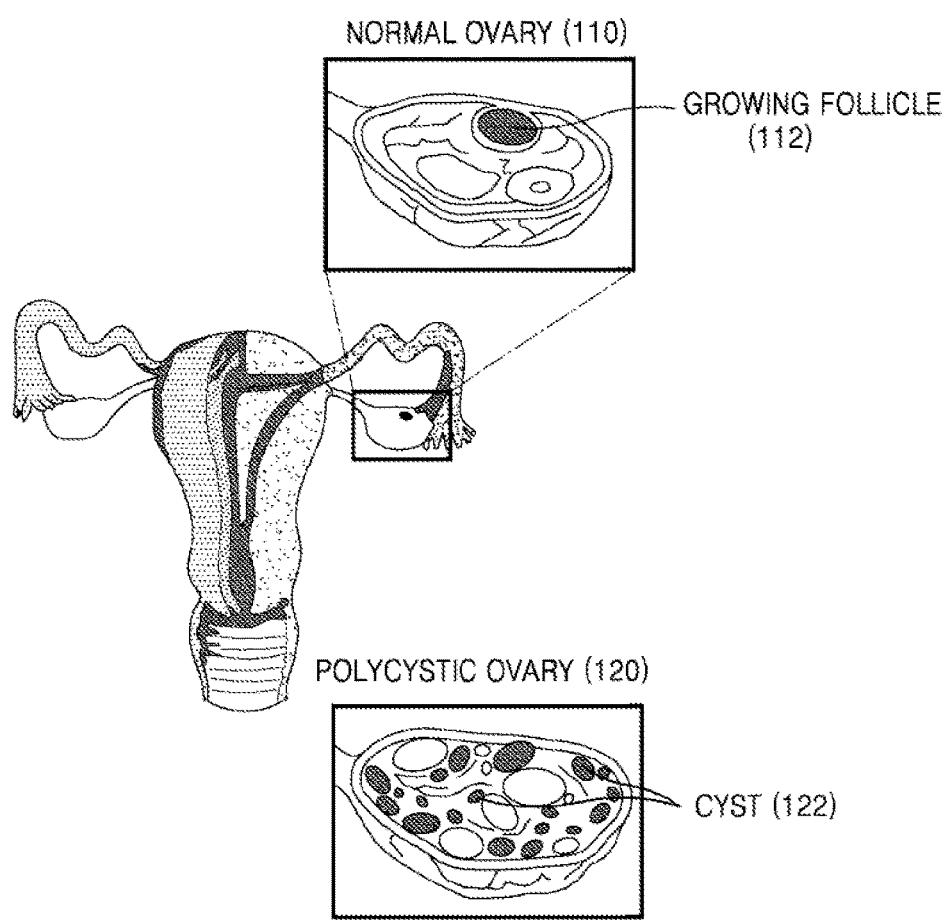
FIG. 1 is a schematic view of a normal ovary and a polycystic ovary.
Figure 2:
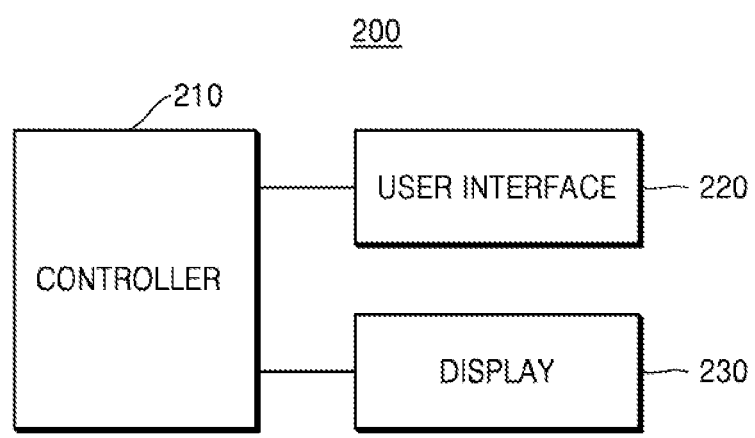
FIG. 2 is a schematic block diagram of a configuration of an ultrasound system according to an embodiment.

FIG. 2 is a schematic block diagram of a configuration of an ultrasound system 200 according to an embodiment. According to an embodiment, the ultrasound system 200 includes a controller 210, a user interface 220, and a display 230.

The display 230 displays an ultrasound image obtained from an object. According to an embodiment, the ultrasound system 200 obtains ultrasound data from the object and generates 3-dimensional (3D) volume data that includes a plurality of voxels by using the obtained ultrasound data. The display 230 may display a 3D ultrasound image generated from the volume data, a 2-dimensional (2D) image of a cross-section of the volume data, or simultaneously display a combination thereof. Each of the plurality of voxels in the 3D volume data may include image data. The image data of each voxel may include brightness values or the intensity of the obtained ultrasound data.

According to an embodiment, the display 230 may also display a plurality of labels generated from the ultrasound image. According to an embodiment, the ultrasound system 200 may generate a label by using the image data of each voxel in the 3D volume data. According to an embodiment, based on a predetermined first threshold value, the ultrasound system 200 may extract voxels having brightness values that are lower than the first threshold value or voxels having brightness values that are higher than the first threshold value from the plurality of voxels in the volume data. Then, the ultrasound system 200 may distinguish regions formed by adjacent voxels from among the extracted voxels. The ultrasound system 200 may generate labels of the regions and the display 230 may display the labels generated by the ultrasound system 200. The ultrasound system 200 may generate the labels based on various image data in each voxel other than a brightness value. According to an embodiment, the ultrasound system 200 may generate a plurality of labels based on the intensity of ultrasound data in each voxel.

For example, if the object is the ovary, the ultrasound system 200 may generate a plurality of labels based on 3D regions that have a brightness value that is the same or lower than a predetermined brightness value, that is, which have a high probability of being regions corresponding to follicles in volume data of the ovary. The display 230 may display the generated plurality of labels. In this case, the display 230 may display a 3D ultrasound image of the volume data and a plurality of labels that indicate a plurality of follicles having 3D shapes.

The plurality of labels may be displayed by using a certain color so that they may be distinguished in the 3D ultrasound image. Also, along with an image of a certain cross-section of the 3D volume data, the display 230 may display a certain plane region of a label through which the certain cross-section passes from among the plurality of labels. The display 230 may display a boundary of a label so that the label is distinguished in a cross-section image. The display 230 may display the boundary of the label or an entire area corresponding to the label by using a certain color.

The user interface 220 may receive a signal corresponding to an input of a user. The user interface 220 according to embodiments may receive a selection signal for selecting at least one label from the plurality of labels. This will be described in detail below with reference to FIG. 7.

Also, the user interface 220 may receive an adjustment signal for adjusting a threshold value, which is used by the ultrasound system 200 to generate a label from the volume data, from the user. According to an embodiment, if a threshold value determined in the ultrasound system 200 is a first threshold value, the user interface 220 may receive a signal for increasing or decreasing the first threshold value. For example, if a threshold value determined in the ultrasound system 200 is 10 (first threshold value), the user interface 220 may receive an input for increasing the threshold value, and the ultrasound system 200 may change the threshold value to 10.1 (second threshold value). According to another embodiment, when the threshold value determined in the ultrasound system 200 is the first threshold value, the user interface 220 may directly receive a second threshold value from the user. As another example, if the threshold value determined in the ultrasound system 200 is 10 (first threshold value), the user interface 220 may receive a setting signal for directly inputting 10.1 (second threshold value) as a new threshold value.

Based on a new threshold value determined based on the adjustment signal received by the user interface 220, the controller 210 may control the ultrasound system 200 so that new labels are generated from the volume data. Specifically, when a threshold value determined in the ultrasound system 200 is changed from a first threshold value to a second threshold value based on an adjustment signal received by the user interface 220, the controller 210 may control the display 230 so that labels that are newly generated based on the second threshold value are displayed.

According to an embodiment, the controller 210 may control the display 230 so that some of the labels that are newly generated based on the second threshold value are displayed. According to an embodiment, a first label may be selected according to a selection signal that is input to the user interface 220 from the plurality of labels displayed on the display 230 based on the first threshold value, and the threshold value may be changed to the second threshold value based on the adjustment signal that is input to the user interface 220. Then, the controller 210 may control the display 230 so that a second label, which corresponds to the first label from among a plurality of new labels generated based on the second threshold value, is displayed on a region corresponding to the first label. In other words, the display 230 may be controlled so that a second label, which is generated based on the second threshold value, is displayed on a region corresponding to the first label instead of the first label that is generated based on the first threshold value. In this case, the controller 210 may control the display 230 so that the remaining labels generated based on the first threshold value are displayed on regions corresponding to non-selected labels. Embodiments in which new labels are displayed based on the second threshold value will be described in detail below with reference to FIGS. 8A to 8D, 9, and 10.

Figure 3:
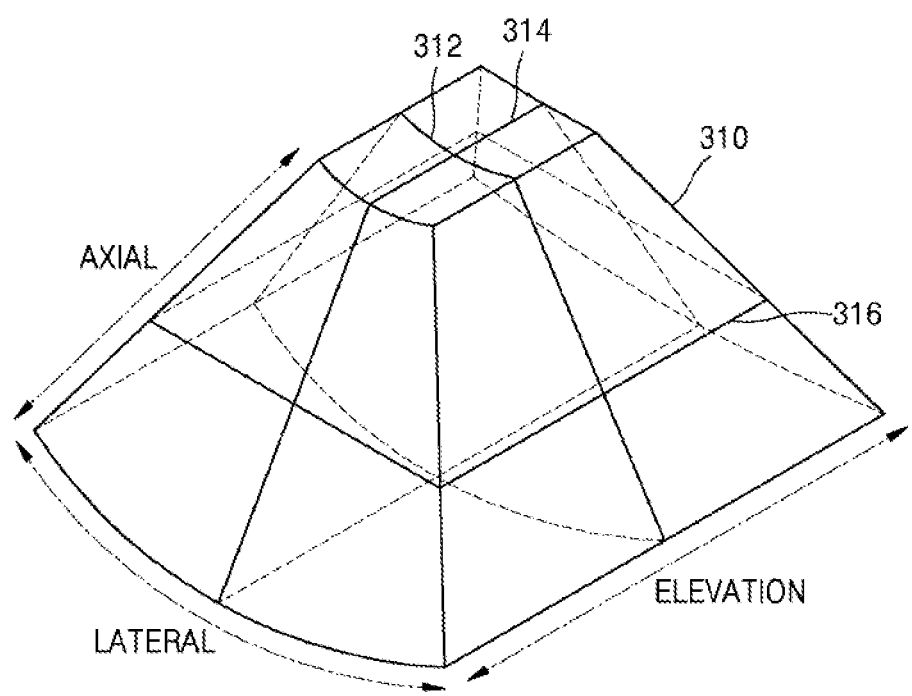
FIG. 3 is a view of volume data according to an embodiment.

FIG. 3 is a view of volume data 310 according to an embodiment. The ultrasound system 200 may generate the volume data 310 including a plurality of voxels as shown in FIG. 3 by using the ultrasound data obtained from the object.

Referring to FIG. 3, reference numerals 312, 314, and 316 respectively indicate a sagittal view, a coronal view, and an axial view that are perpendicular to each other. Also, in FIG. 3, an axial direction is a proceeding direction of an ultrasound signal with respect to a converter of an ultrasound probe, a lateral direction is a moving direction of a scan line, and an elevation direction is a moving direction of a frame (that is, a scanning area), which corresponds to a depth direction of a 3D ultrasound image.

Figure 4:
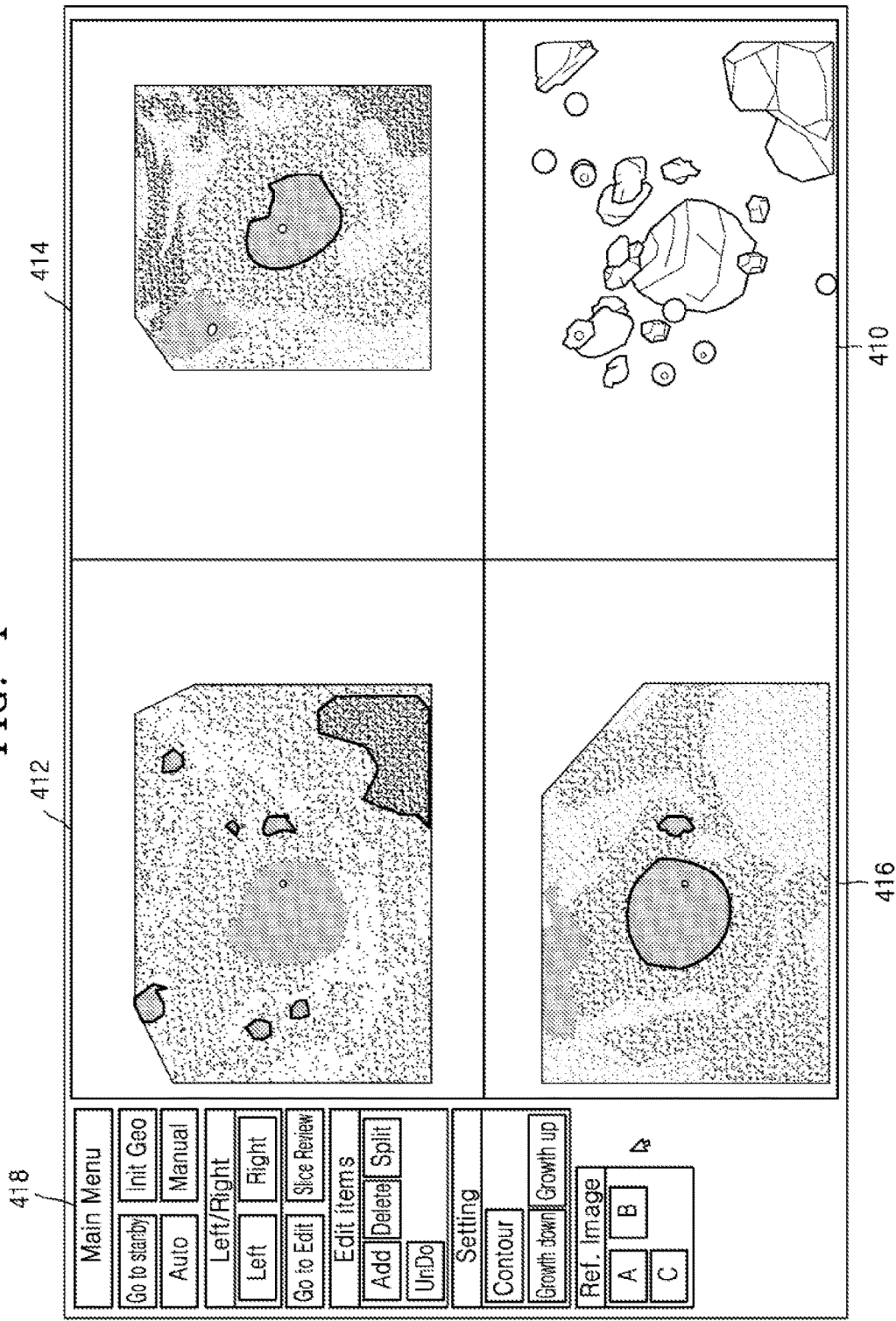
FIG. 4 is an exemplary view of a user interface and ultrasound images that 3-dimensionally and 2-dimensionally display volume data, according to an embodiment.

FIG. 4 is an exemplary view of a user interface 418 and ultrasound images (410, 412, 414, and 416) that 3-dimensionally and 2-dimensionally display volume data, according to an embodiment. A lower right image 410 displays 3D labels generated in the volume data. An upper left image 412, an upper right image 414, and a lower left image 416 display ultrasound images generated according to different cross-sections of the volume data. Also, the upper left image 412, the upper right image 414, and the lower left image 416 display labels that indicate regions where the cross-sections meet with the 3D labels generated in the volume data. When the upper left image 412, the upper right image 414, and the lower left image 416 display the labels, only boundaries of the labels may be displayed.

According to an embodiment, the lower right image 410 displays a 3D ultrasound image generated from the volume data 310 of FIG. 3. Also, an ultrasound image showing the sagittal view 312, an ultrasound image showing the coronal view 314, and an ultrasound image showing the axial view 316 may be displayed on the upper left image 412, the upper right image 414, and the lower left image 416, respectively.

Also, the user interface 418 of FIG. 4 may receive an input necessary for editing the ultrasound images (410, 412, 414, and 416) from the user.

Figure 5A:
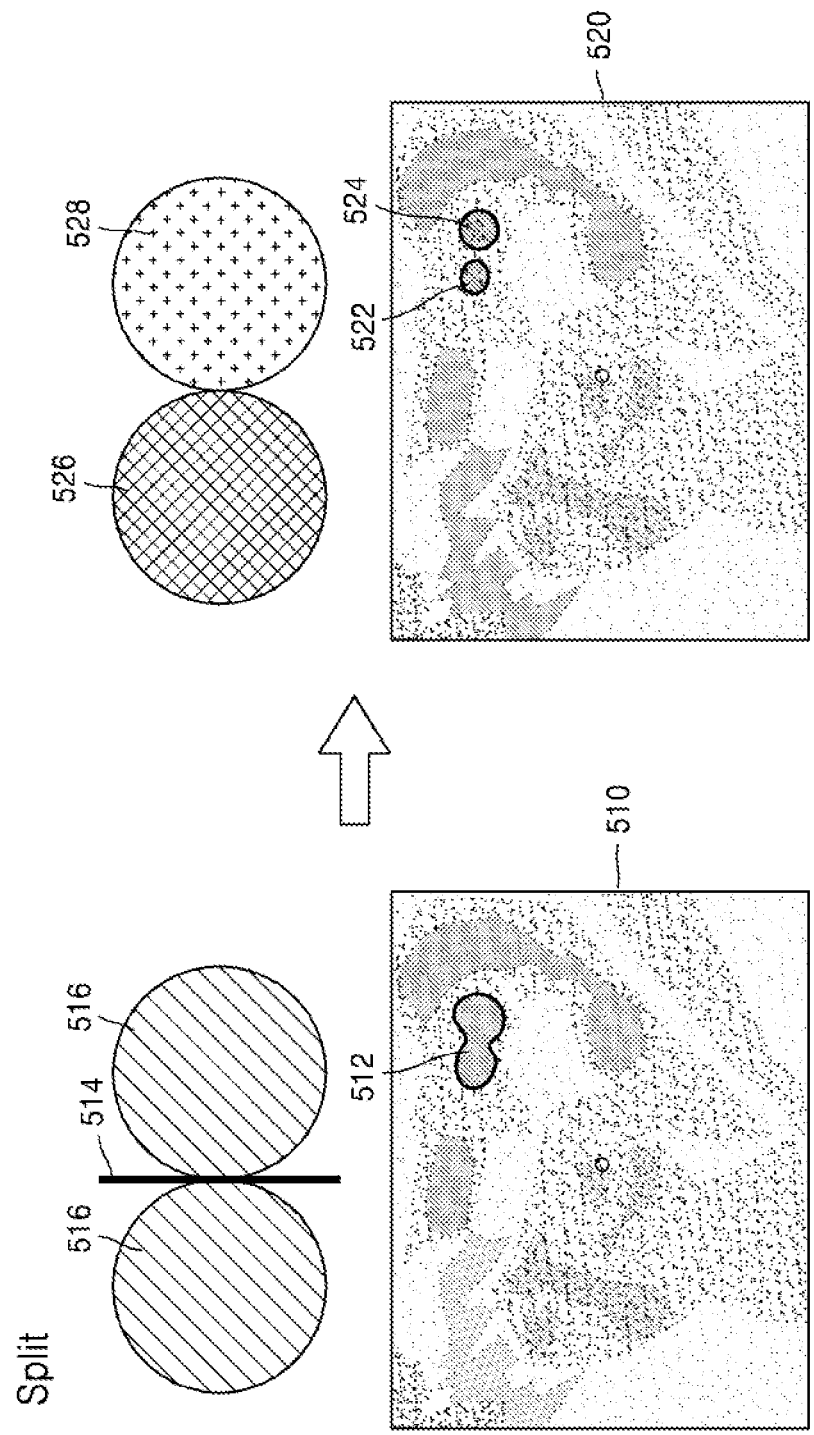

FIGS. 5A and 5B are schematic views of a method of splitting or merging labels generated in ultrasound images.

Referring to FIG. 5A, the ultrasound system 200 displays an ultrasound image 510 and a plurality of labels including a certain label 512. Based on a shape, a position, etc. of the certain label 512, the user may determine that the certain label 512 should have been separately displayed as two different labels but is merged into a single label due to technical errors or inaccuracy. According to an embodiment, the ultrasound system 200 may receive a user input for splitting the certain label 512 from the user. When a FIG. 516 formed by two connected circles indicate the certain label 512, the ultrasound system 200 may receive a splitting line 514 for splitting the two circles from the user. Accordingly, the ultrasound system 200 may split the FIG. 516 indicating the certain label 512 and display two different labels 526 and 528. The two circles in the FIG. 516 that indicate the certain label 512 may substantially maintain their shapes, sizes, and positions, but may be shown in different colors or patterns to indicate that they have been split into the two different labels 526 and 528.

Referring to FIG. 5B, the ultrasound system 200 displays an ultrasound image 530 and a plurality of labels including two certain labels 532 and 534. Based on shapes, positions, etc. of the two certain labels 532 and 534, the user may determine that the two certain labels 532 and 534 should have been displayed as a single label but are split into two different labels due to technical errors or inaccuracy. According to an embodiment, the ultrasound system 200 may receive a user input for merging the two certain labels 532 and 534 from the user. When two circles 537 and 538 respectively indicate the two certain labels 532 and 534, the ultrasound system 200 may receive a connecting line 536 for merging the two circles 537 and 538 from the user. Accordingly, the ultrasound system 200 may merge the two certain labels 532 and 534 and display a single label 544. The two circles 537 and 538 that indicate the two certain labels 532 and 534 may substantially maintain their shapes, sizes, and positions, but may be shown in the same color or pattern to indicate that they have been merged into the single label 544.

Figure 6:
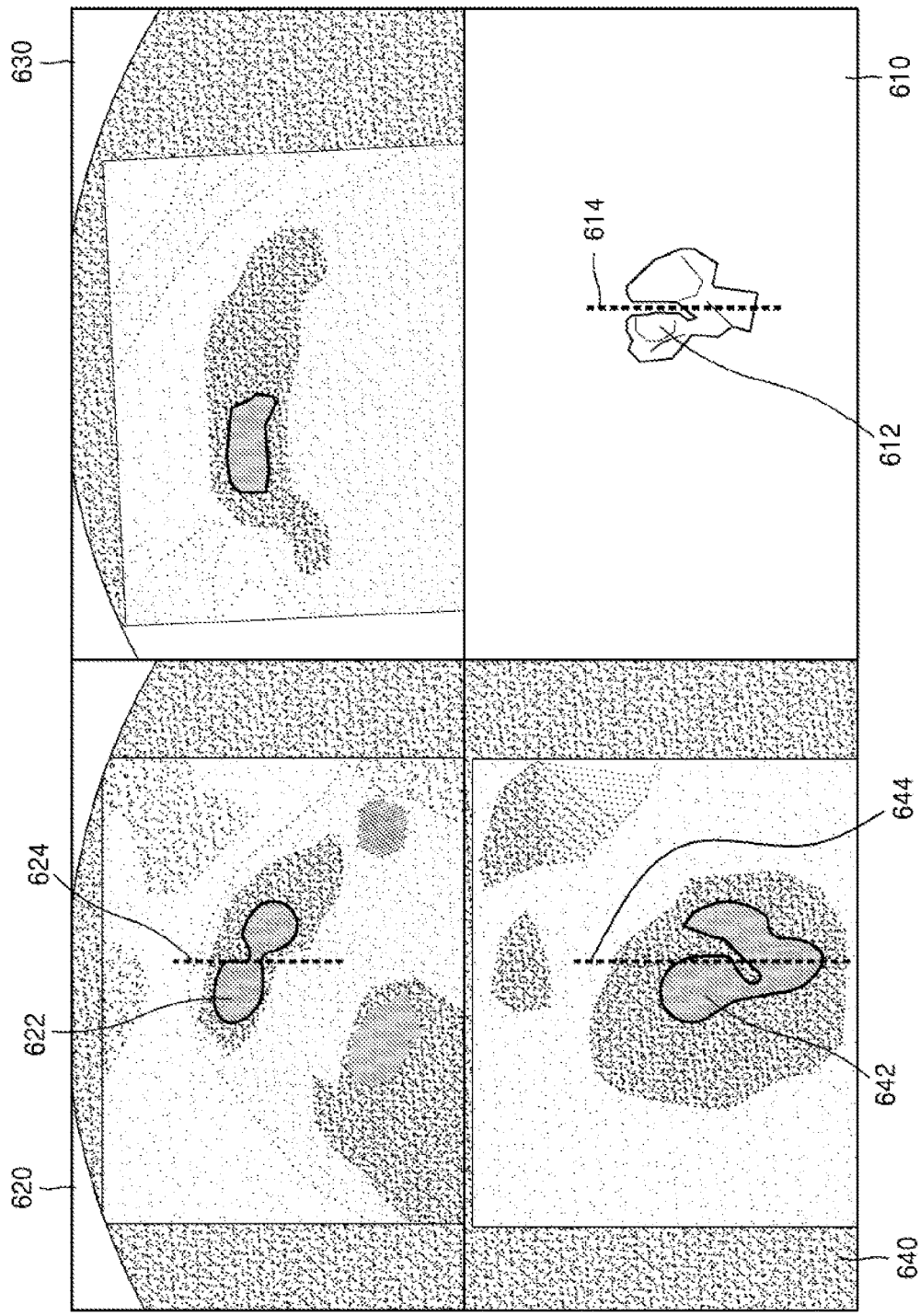
FIG. 6 is a view of a method of splitting or merging labels generated in ultrasound images shown in actual ultrasound images.

FIG. 6 is a view of a method of splitting or merging labels generated in ultrasound images shown in actual ultrasound images.

Referring to FIG. 6, a lower right image 610 3-dimensionally displays a label 612 generated in 3D volume data. An upper left image 620, an upper right image 630, and a lower left image 640 display ultrasound images generated according to certain cross-sections of the volume data. The upper left image 620 includes a label 622, the upper right image 630 includes a label 632, and a lower left image 640 includes a label 642. Based on respective locations and shapes of the labels 612, 622, and 642 in the ultrasound images, the user may determine that each of the labels 612, 622, and 642 should have been split into two but are wrongly displayed as a single label. Accordingly, the ultrasound system 200 may receive splitting lines 614, 624, and 644 for splitting the labels 612, 622, and 642 from the user.

However, considering that 3D labels generated in the volume data may have various 3-dimensional or geometrical structures, it may be difficult for the user to exactly split the labels 612, 622, and 642 in a desired way by only using the splitting lines 614, 624, and 644 respectively input to the lower right image 610, the upper left image 620, and the lower left image 640 as shown in FIG. 6. According to the embodiments, this shortcoming may be overcome. This will be described in detail below.

FIGS. 7A to 7D are views of a method of selecting a label to be edited from labels generated in an ultrasound image, according to an embodiment.

Figure 7A:
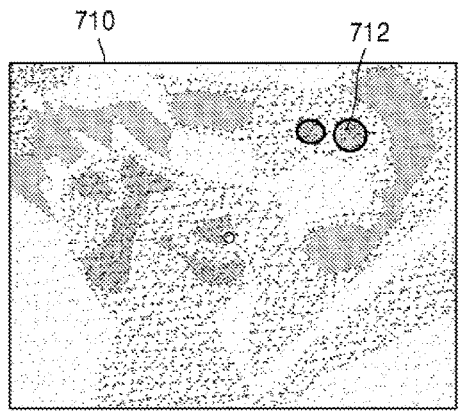
FIGS. 7A to 7D are views of a method of selecting a label to be edited from labels generated in an ultrasound image, according to an embodiment.

Referring to FIG. 7A, in order to select a label 712 displayed on an ultrasound image 710, a user interface may receive an input for selecting a point inside the label 712 from the user. According to an embodiment, the user interface may select the point by moving a mouse pointer to the point inside the label 712. According to another embodiment, the user interface may receive a touch panel input that selects the point inside the label 712. The point inside the label 712 may correspond to a voxel in volume data which is located inside a region corresponding to the label 712. Since each voxel in the volume data may have coordinates information, an ultrasound system may detect a location of a voxel selected based on certain coordinates information of a voxel selected by a user input, or a 3D label including the selected voxel. According to another embodiment, the user interface may select the label 712 by selecting one identifier from a plurality of identifiers that respectively indicate a plurality of labels. Other than the methods described above, various input methods that are well-known to one of ordinary skill in the art may be used to select the point inside the label 712.

Figure 7B:
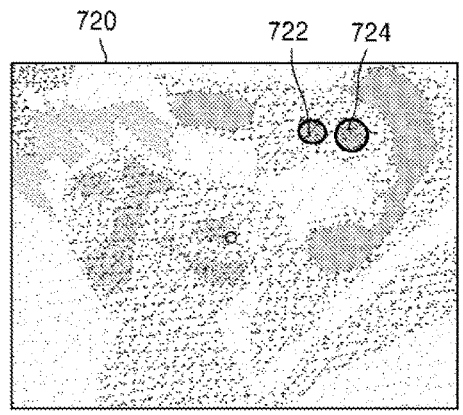

Referring to FIG. 7B, in order to select two labels 722 and 724 displayed on an ultrasound image 720, a user interface may receive an input for selecting points inside the labels 722 and 724 from the user. According to an embodiment, the user interface may receive an input for selecting the point inside the label 722 and then, receive an input for selecting the point inside the label 724. The user interface may receive user inputs for selecting the labels 722 and 724 by using the methods described with reference to FIG. 7A.

Figure 7C:
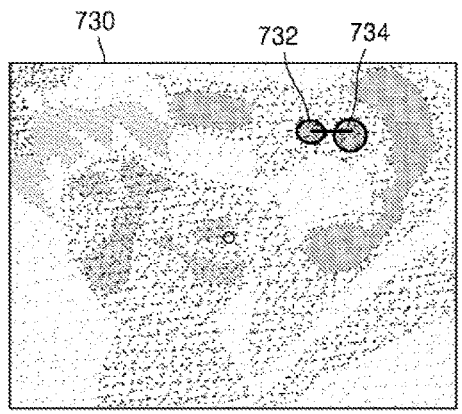
Figure 7D:
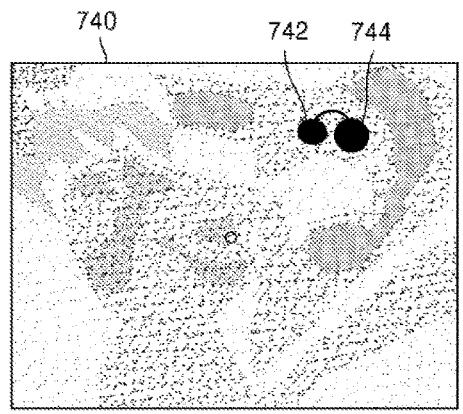
Figure 10:
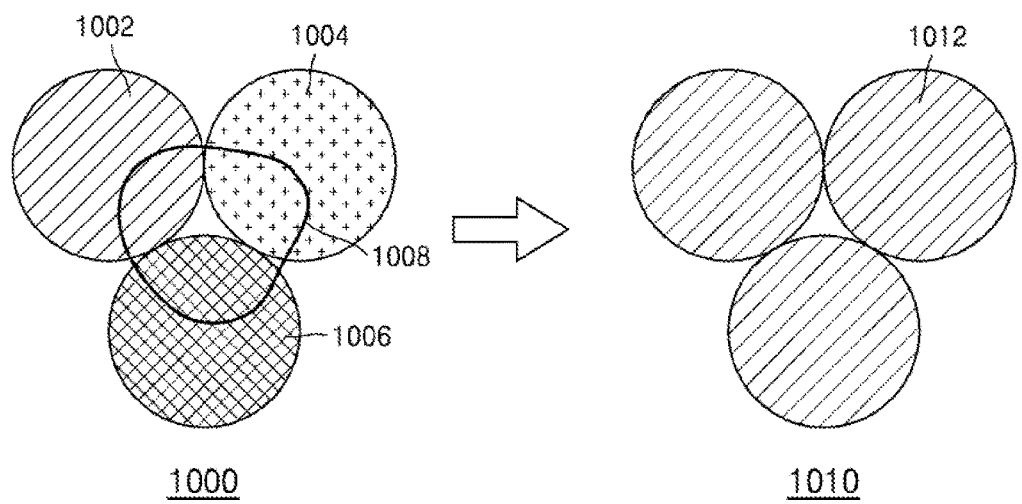
FIG. 10 is a view of a process of three labels being selected and merged into a single label, according to an embodiment.

Referring to FIGS. 7C and 7D, in order to select two labels 732 and 734 displayed on an ultrasound image 730, a user interface may receive a user input for inputting a straight line or a curved line crossing the two labels 732 and 734 from the user. As described with reference to FIG. 7A, the user input may be moving the mouse pointer, dragging, or a touch input of the user. Referring to FIG. 10, according to an embodiment, the user interface may receive an input 1008 of a curved line or a figure drawn with a curved line so as to select three labels 1002, 1004, and 1006.

FIGS. 8A to 8D are views of processes of splitting, merging, or deleting a generated label or newly generating a label according to an input of the user, according to an embodiment.

FIG. 8A illustrates a process of editing via which two split labels are merged into a single layer by a selection of the user and change in a threshold value. Referring to FIG. 8A, a left side 810 shows ultrasound images 811 and 815 and labels 812, 814, 816, and 818 generated based on a first threshold value of volume data obtained from an object. A right side 820 shows ultrasound images 821 and 825 and labels 822 and 826 generated based on a second threshold value of the same volume data.

According to an embodiment, when generating the ultrasound images 821 and 825 and the labels 822 and 826 based on the second threshold value, the ultrasound system 200 may maintain the ultrasound images 811 and 815 that are based on the first threshold value and newly generate the labels 822 and 826 based on the second threshold value. Alternatively, according to another embodiment, when displaying an ultrasound image and a label on the display 230, the ultrasound system 200 may not generate a new ultrasound image based on the second threshold value but display an ultrasound image generated based on the first threshold value as it is, newly generate only a label but not an ultrasound image based on the second threshold value, and display a portion of the label that is newly generated.

Although a plurality of labels other than the labels 812, 814, 816, and 818 may be displayed on the ultrasound images 811 and 815, only the labels 812, 814, 816, and 818 are displayed for convenience. The user may select the labels 812, 814, 816, and 818 from the plurality of labels that are displayed. The ultrasound image 815 3-dimensionally displays the labels 816 and 818 that are generated based on the volume data, and the ultrasound image 811 displays the labels 812 and 814 with a cross-sectional ultrasound image. Although the ultrasound image 811 and the labels 812 and 814 are 2-dimensionally displayed, as the ultrasound image 811 and the labels 812 and 814 are located at a certain cross-section of the volume data, points included in the ultrasound image 811 and the labels 812 and 814 may have 3D coordinates. In addition, the labels 812 and 814 on the ultrasound image 811 may respectively correspond to the labels 816 and 818 on the ultrasound image 815.

According to an embodiment, from the user, a user interface may receive a user input for selecting the labels 812 and 814 from the plurality of labels on the ultrasound image 811 or selecting the labels 816 and 818 from the plurality of labels on the ultrasound image 815. In addition, the user interface may receive an adjustment signal for adjusting the first threshold value to generate a new label from the user.

The ultrasound system 200 may determine the second threshold value for generating a new label according to an input of the adjustment signal. When the second threshold value is determined, the ultrasound system 200 may generate new labels based on the second threshold value by using the volume data.

According to an embodiment, labels are generated by using voxels having brightness values that are the same as or lower than a certain threshold value. When the second threshold value is higher than the first threshold value, labels generated based on the second threshold value include labels generated based on the first threshold value. Also, the labels generated based on the second threshold value are larger than the labels generated based on the first threshold value.

For example, if the labels 816 and 818 are generated based on voxels in the volume data having lower brightness values than the first threshold value, a certain label generated based on the second threshold value in regions corresponding to the labels 816 and 818 may include all voxels included in the labels 816 and 818 and additionally, voxels that were not included in the labels 816 and 818 generated based on the first threshold value. For example, a label generated based on the second threshold value in the regions corresponding to the labels 816 and 818 may additionally include voxels between the labels 816 and 818. Therefore, when the second threshold value is greater than a certain value, the label 826 that is one connected label may be generated in the regions corresponding to the labels 816 and 818. In other words, when a threshold value that is a basis for generating a label is changed to the second threshold value, the labels 816 and 818 generated based on the first threshold value may be displayed as if the labels 816 and 818 are merged into the label 826 that includes the labels 816 and 818. In this case, the label 826 is displayed on the 3D ultrasound image 825, and the label 822 that corresponds to the 3D label 826 on the ultrasound image 821 that is a cross-section image.

According to an embodiment, when displaying a label generated based on the second threshold value, the ultrasound system 200 may not replace all labels generated based on the first threshold value with labels generated based on the second threshold value, but only replace a label selected by the user from the labels generated based on the first threshold value with the label generated based on the second threshold value.

For example, a plurality of labels, including the labels 812 and 814, may be displayed on the ultrasound image 811 based on the first threshold value. When the user interface 220 receives an input for selecting the labels 812 and 814 from the user, the label 222 may replace the labels 812 and 814 and be displayed on the combined region on the ultrasound image 821 which correspond to the labels 812 and 814 while labels that are not selected from the ultrasound image 811 are displayed as they are. By using the same method, labels may also be replaced and displayed on the ultrasound images 815 and 825, in which labels are displayed 3-dimensionally.

By using the method above, the user may select at least two labels that are adjacent and should be merged from a plurality of labels displayed on the ultrasound image 811, adjust a threshold value so that the selected at least two labels are merged into and displayed as a single label, and maintain remaining labels to be displayed as they are.

Figure 8B:
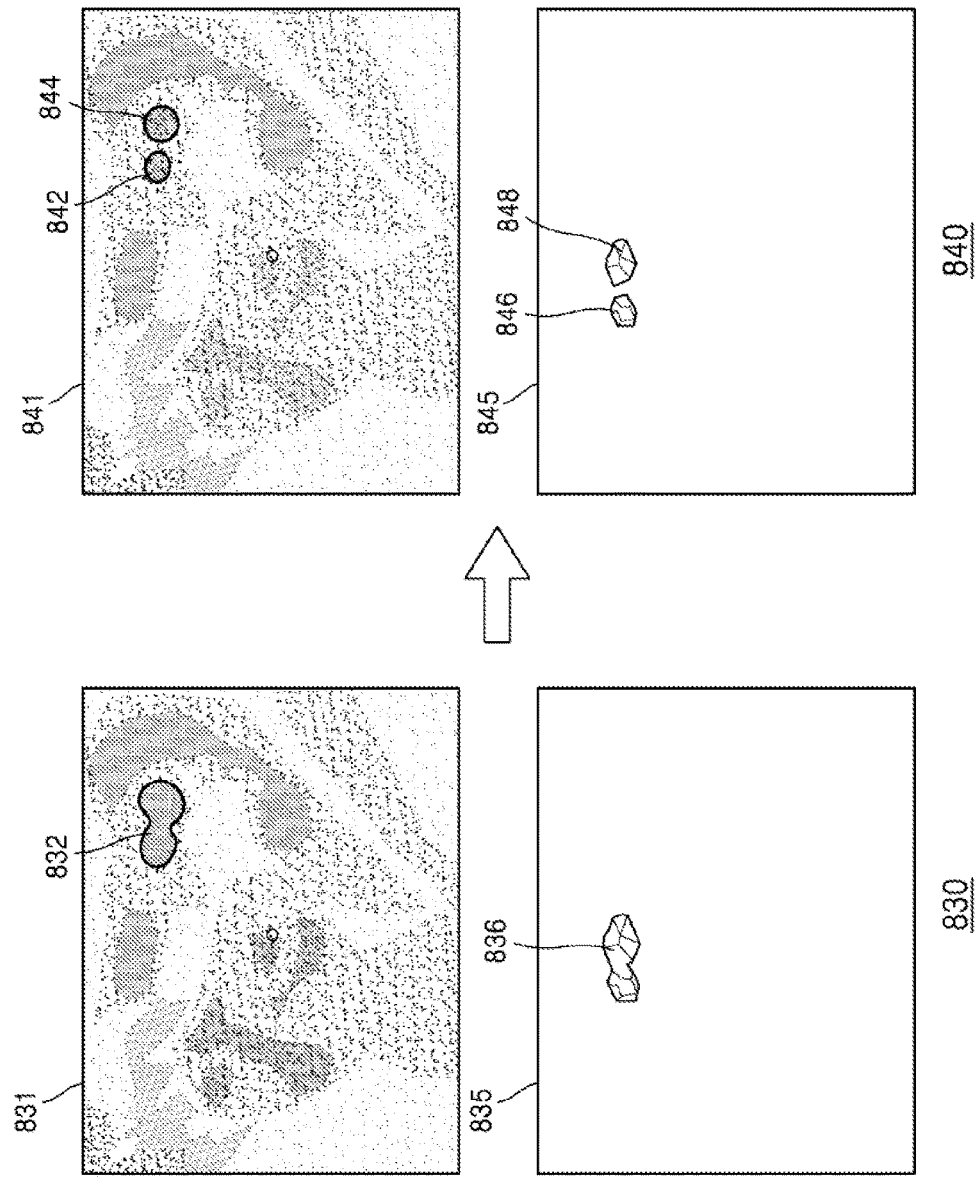

FIG. 8B illustrates a process that is opposite to the process of editing ultrasound images and labels shown in FIG. 8A. Referring to FIG. 8B, a left side 830 shows ultrasound images 831 and 835 and labels 832 and 836 generated based on a first threshold value, and a right side 840 shows ultrasound images 841 and 845 and labels 842, 844, 846, and 848 generated based on a second threshold value. Since a corresponding relationship between the ultrasound images 835 and 845 and the labels 836, 846, and 848 that are 3-dimensionally displayed and the ultrasound images 831 and 841 and the labels 832, 836, 842, 844, 846, and 848 that are displayed with respect to certain cross-sections are the same as that described above, the detailed description thereof will be omitted.

According to an embodiment, a user interface may receive a user input for selecting the label 832 from a plurality of labels on the ultrasound image 831 or selecting the label 836 from a plurality of labels on the ultrasound image 835, from the user. In addition, the user interface may receive an adjustment signal for adjusting the first threshold value to generate a new label from the user.

The ultrasound system 200 may determine the second threshold value for generating a new label according to an input of the adjustment signal. When the second threshold value is determined, the ultrasound system 200 may generate new labels based on the second threshold value by using volume data.

According to an embodiment, labels are generated by using voxels having brightness values that are the same or lower than a certain threshold value. When the second threshold value is lower than the first threshold value, labels generated based on the second threshold value are smaller than labels generated based on the first threshold value.

For example, if the label 836 is generated based on voxels in the volume data having lower brightness values than the first threshold value, a certain label generated in a region corresponding to the label 836 based on the second threshold value that is lower than the first threshold value may only include some voxels included in the label 836. According to an embodiment, a label generated based on the second threshold value in the region corresponding to the label 836 may not include some voxels inside the label 836, and thus, the labels 846 and 848, which are split by two, may be generated in the region corresponding to the label 836. In other words, by reducing a threshold value, the labels 846 and 848, which are split by two, may be displayed based on the second threshold value in the region where only the label 836 had been displayed based on the first threshold value.

According to an embodiment, as described above, when displaying a label generated based on the second threshold value, the ultrasound system 200 may not replace all labels generated based on the first threshold value with labels generated based on the second threshold value, but only replace a label selected by the user from the labels generated based on the first threshold value with the label generated based on the second threshold value.

For example, a plurality of labels, including the label 832, may be displayed on the ultrasound image 831 based on the first threshold value. When the user interface 220 receives an input for selecting the label 832 from the user, the labels 842 and 844 may replace the label 832 and be displayed on a region on the ultrasound image 841 which corresponds to the label 832 while labels that are not selected from the ultrasound image 831 are displayed as they are. By using the same method, labels may also be replaced and displayed on the ultrasound images 835 and 845, in which labels are displayed 3-dimensionally.

By using the method above, the user may select a label that should be split from a plurality of labels displayed on the ultrasound image 831, adjust a threshold value so that the selected label is split into and displayed as at least two labels, and maintain remaining labels to be displayed as they are.

Figure 8C:
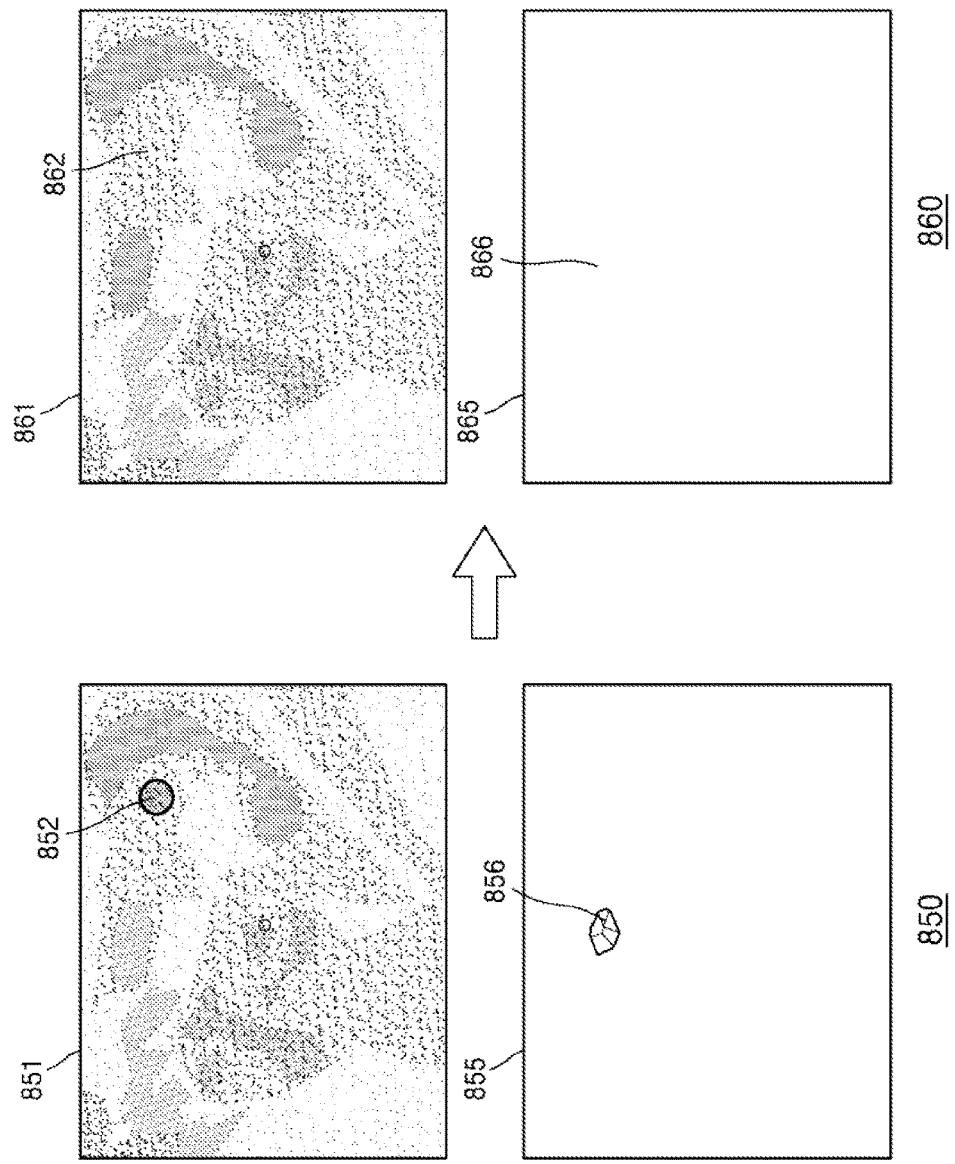

FIG. 8C illustrates a process of not displaying a selected label, that is, deleting the selected label. Referring to FIG. 8C, a user interface may receive a user input for selecting a label 852 from a plurality of labels displayed on an ultrasound image 851, selecting a label 856 from a plurality of labels displayed on an ultrasound image 855, or selecting both, from the user. In addition, the user interface may receive an adjustment signal for adjusting a first threshold value from the user. The ultrasound system 200 may determine a second threshold value for generating a new label according to an input of the adjustment signal. When the second threshold value is determined, the ultrasound system 200 may generate new labels based on the second threshold value by using volume data.

According to an embodiment, if the label 856 is generated based on voxels in the volume data having brightness values that are the same as or lower than the first threshold value, brightness values of voxels included in the label 856 may all be greater than the second threshold value (that is smaller than the first threshold value). In this case, when a threshold value, which is a basis for generating a label according to an input of the user, is determined as the second threshold value, a label may not be generated on a region of an ultrasound image 861, which corresponds to a region where the label 856 is displayed.

According to an embodiment, as described above, the ultrasound system 200 may only delete a label selected by the user from a plurality of labels generated based on the first threshold value. For example, a plurality of labels, including the label 852, may be displayed on the ultrasound image 851 based on the first threshold value. When the user interface 220 receives an input for selecting the label 852 from the user, a label is not displayed on a region on the ultrasound image 861 which corresponds to the label 852 while labels that are not selected from the ultrasound image 851 are displayed as they are. By using the same method, labels may also be deleted from the ultrasound image 855 and an ultrasound image 865, in which labels are displayed 3-dimensionally.

Figure 8D:
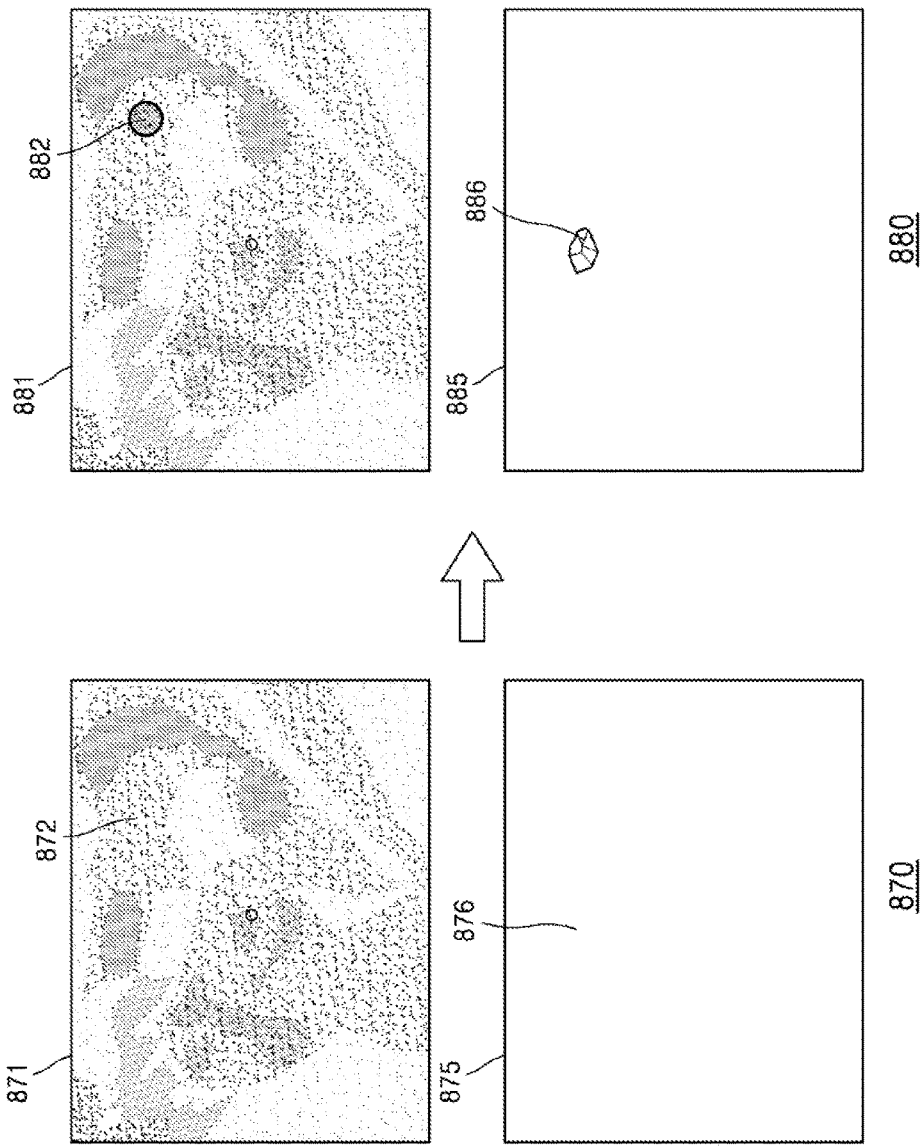

FIG. 8D illustrates a process that is opposite to the process shown in FIG. 8C, that is, a process of newly generating and displaying a label in a region where a label has not been generated. Referring to FIG. 8D, a user interface may receive a user input for selecting a point in a region of an ultrasound image 871 where a label is not generated, selecting a point of an ultrasound image 875 where a label is not generated, or selecting both, from the user. In addition, the user interface may receive an adjustment signal for adjusting a first threshold value from the user. The ultrasound system 200 may determine a second threshold value for generating a new label according to an input of the adjustment signal. When the second threshold value is determined, the ultrasound system 200 may generate new labels based on the second threshold value by using volume data According to an embodiment, a brightness value of a voxel that corresponds to a point selected by the user in the ultrasound image 871 or the ultrasound image 875 may be higher than the first threshold value. Therefore, in the case of the first threshold value, the point selected by the user is not included in any label. However, according to an embodiment, the second threshold value determined according to an input of the user may be higher than a brightness value of a voxel selected by the user. Also, other voxels adjacent to the voxel selected by the user may have brightness values that are lower than the second threshold value. In this case, based on the first threshold value, the ultrasound system 200 may newly generate a label 882 and/or a label 886 on a region in an ultrasound image 881 and/or an ultrasound image 885, the region which includes a certain point not displayed on the ultrasound images 871 and 875.

According to an embodiment, as described above, when generating a label in a region where a label had not been generated, the ultrasound system 200 may display existing labels as they are. For example, a plurality of labels may be displayed on the ultrasound image 871 based on the first threshold value. When the user interface 220 receives an input for selecting a point 872 that is not included in any label from the user, on the ultrasound image 881, the label 882 is displayed on a region including the point 872 selected by the user while labels displayed on the ultrasound image 871 remain. By using the same method, labels may also be newly generated on the ultrasound images 875 and 885, in which labels are displayed 3-dimensionally.

Figure 9:
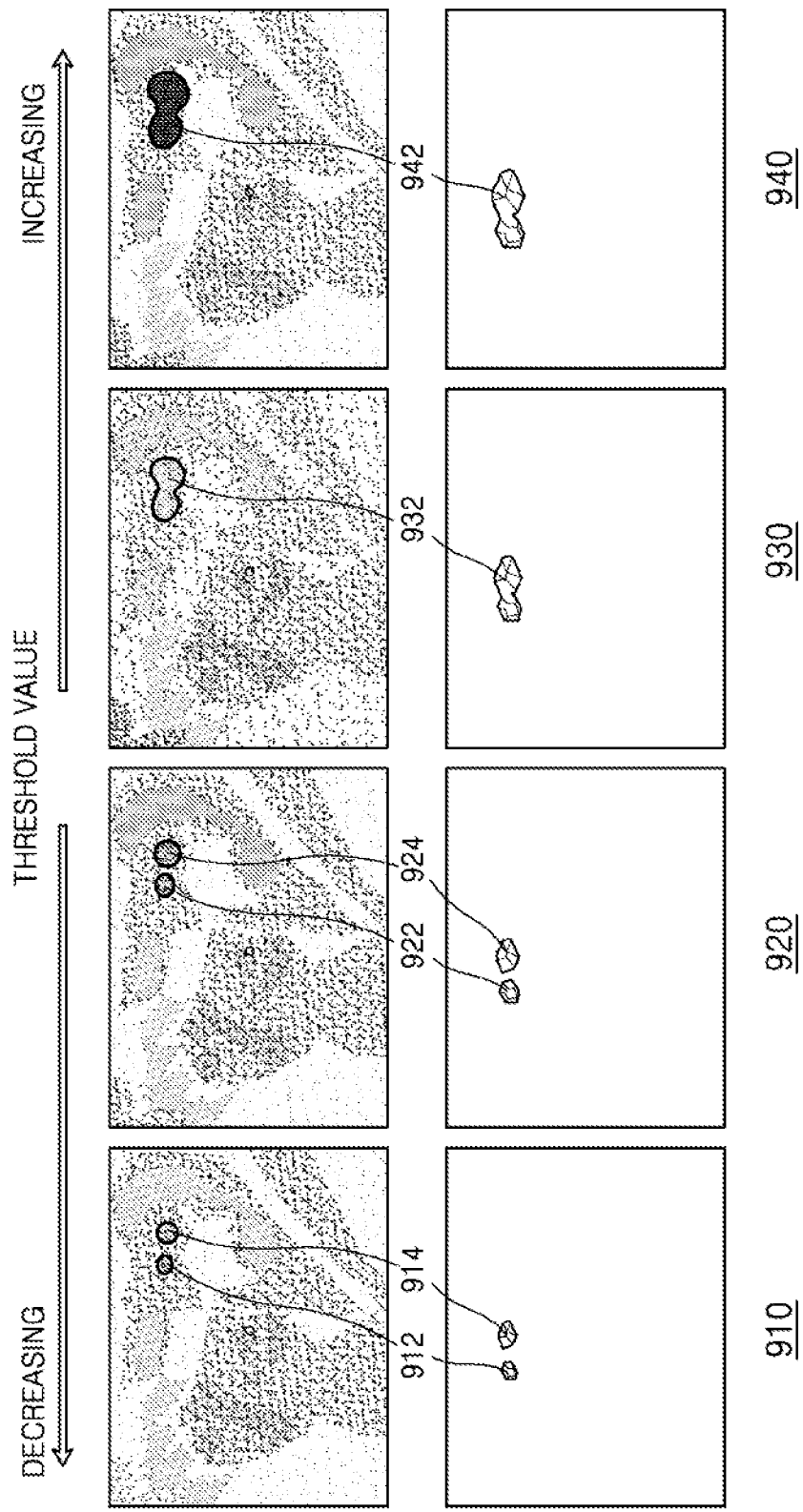
FIG. 9 is a view of a label continuously changing as a threshold value is continuously changed, according to an embodiment.

FIG. 9 is a view of a label continuously changing as a threshold value is continuously changed, according to an embodiment.

A threshold value determined in an ultrasound system may be continuously changed based on an input of the user. An ultrasound image and a label that are displayed may also be continuously changed according to the threshold value determined based on the input of the user. Ultrasound images 910, 920, 930, and 940 represent ultrasound images and labels that are generated based on a certain threshold value consecutively determined according to an input of the user. Although a plurality of labels, including labels 912, 914, 922, 924, 932, and 942, may be displayed on the ultrasound images 910, 920, 930, and 940, only the labels 912, 914, 922, 924, 932, and 942 that are selected by the user are displayed for convenience.

According to an embodiment, if a label is based on voxels having brightness values that are the same or lower than a certain threshold value, the labels 912 and 914 are displayed on the ultrasound image 910 based on the certain threshold value. If the threshold value determined in the ultrasound system is increased according to an input of the user, the labels 922 and 924, which include and are larger than the labels 912 and 914, are displayed on the ultrasound image 920. If the threshold value determined in the ultrasound system is further increased according to an input of the user, the label 932, which is generated by merging the labels 922 and 924, are displayed on a region of the ultrasound image 930, which corresponds to the labels 922 and 924. These processes are the same as those described with reference to FIG. 8A. If the threshold value determined in the ultrasound system is further increased according to an input of the user, the label 942, which includes and is larger than the label 932, is displayed on the ultrasound image 940.

On the contrary, if the threshold value determined in the ultrasound system is reduced according to an input of the user, a label displayed on the ultrasound image 940 may be gradually reduced in size and thus be split. A process of splitting a single label is the same as that described with reference to FIG. 8B.

Figure 11:
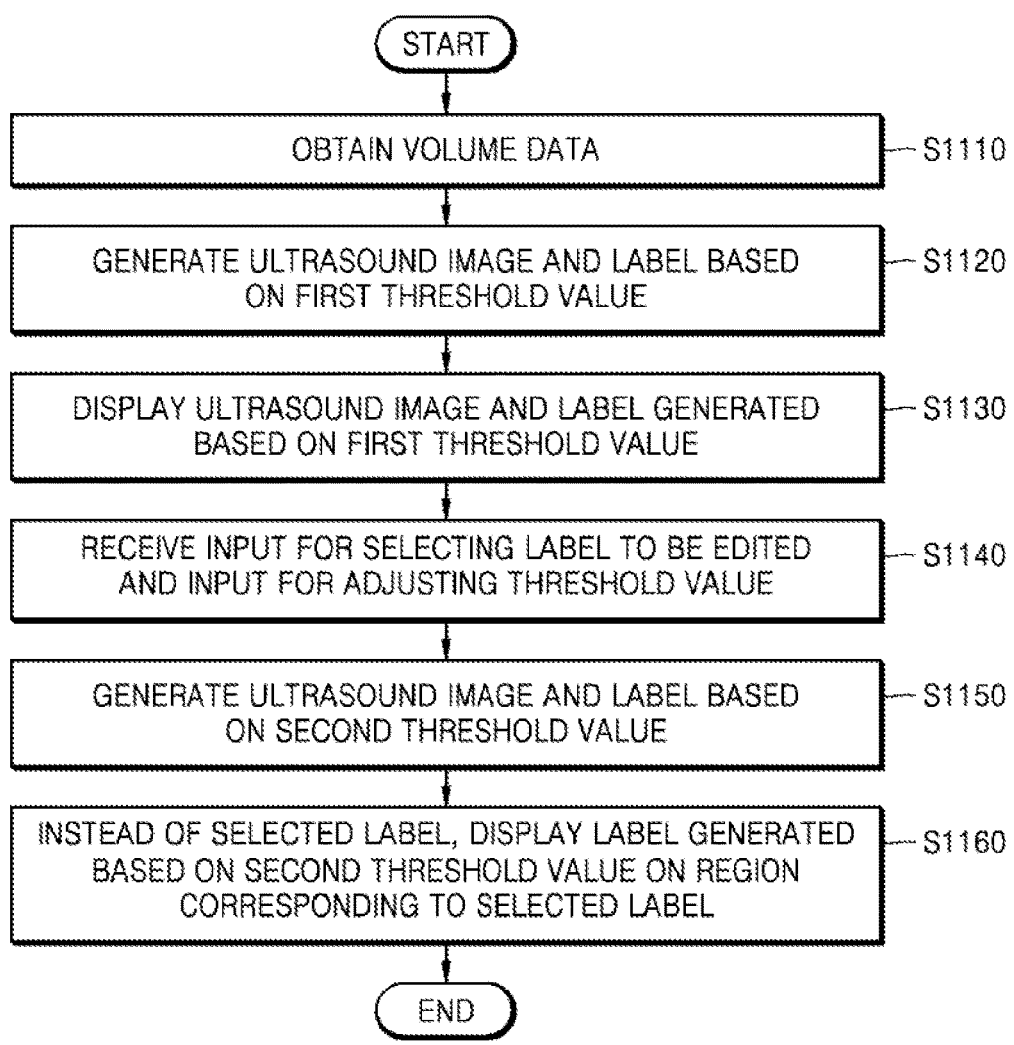
FIG. 11 is a flowchart of a variable editing method of an ultrasound image, according to an embodiment.

FIG. 11 is a flowchart of a variable editing method of an ultrasound image, according to an embodiment.

In operation S1110, the ultrasound system 200 obtains volume data of an object. The volume data is 3D data and includes a plurality of voxels. Each of the plurality of voxels in the volume data includes image data, for example, a brightness value.

In operation S1120, the ultrasound system 200 generates an ultrasound image and a label from the volume data based on a first threshold value. The ultrasound system 200 may generate a 3D image, a 2D image of a certain cross-section of the volume data, or both. The ultrasound system 200 generates the label by using voxels having image data that is the same, higher, or lower than the first threshold value. For example, the ultrasound system 200 may accumulate adjacent voxels from among voxels having brightness values that are the same or lower than the first threshold value and generate a single label.

In operation S1130, the ultrasound system 200 displays the ultrasound image and the label generated based on the first threshold value. The ultrasound system 200 may display a 3D ultrasound image and a 3D label overlapping or a 2D ultrasound image of a certain cross-section and a 2D label overlapping. The ultrasound system 200 may display the label in a different color or pattern or a boundary of the label so that the label may be distinguished from the ultrasound image.

In operation S1140, the ultrasound system 200 receives a user input for selecting a label to be edited and a user input for adjusting a threshold value. The user input for selecting a label may select at least one label from a plurality of displayed labels. According to an embodiment, the user input for selecting a label to be edited may select coordinates corresponding to voxels included in the selected label. According to another embodiment, the user input for selecting a label to be edited may input a line crossing at least one label.

In addition, according to an embodiment, the user input for adjusting a threshold value may change the first threshold value by a certain amount. In this case, the ultrasound system 200 determines a second threshold value based on the user input. According to another embodiment, the user input for adjusting a threshold value may directly input a second threshold value.

In operation S1150, the ultrasound system 200 generates an ultrasound image and a label based on the determined second threshold value.

In operation S1160, the ultrasound system 200 displays the ultrasound image and the label generated based on the second threshold value. According to an embodiment, instead of the label selected according to the user input in operation S1140, the ultrasound system 200 displays a new label generated based on the second threshold value on a region corresponding to the label selected according to the user input in operation S1140. In this case, labels that are not selected according to the user input may be displayed as they are.

Figure 12:
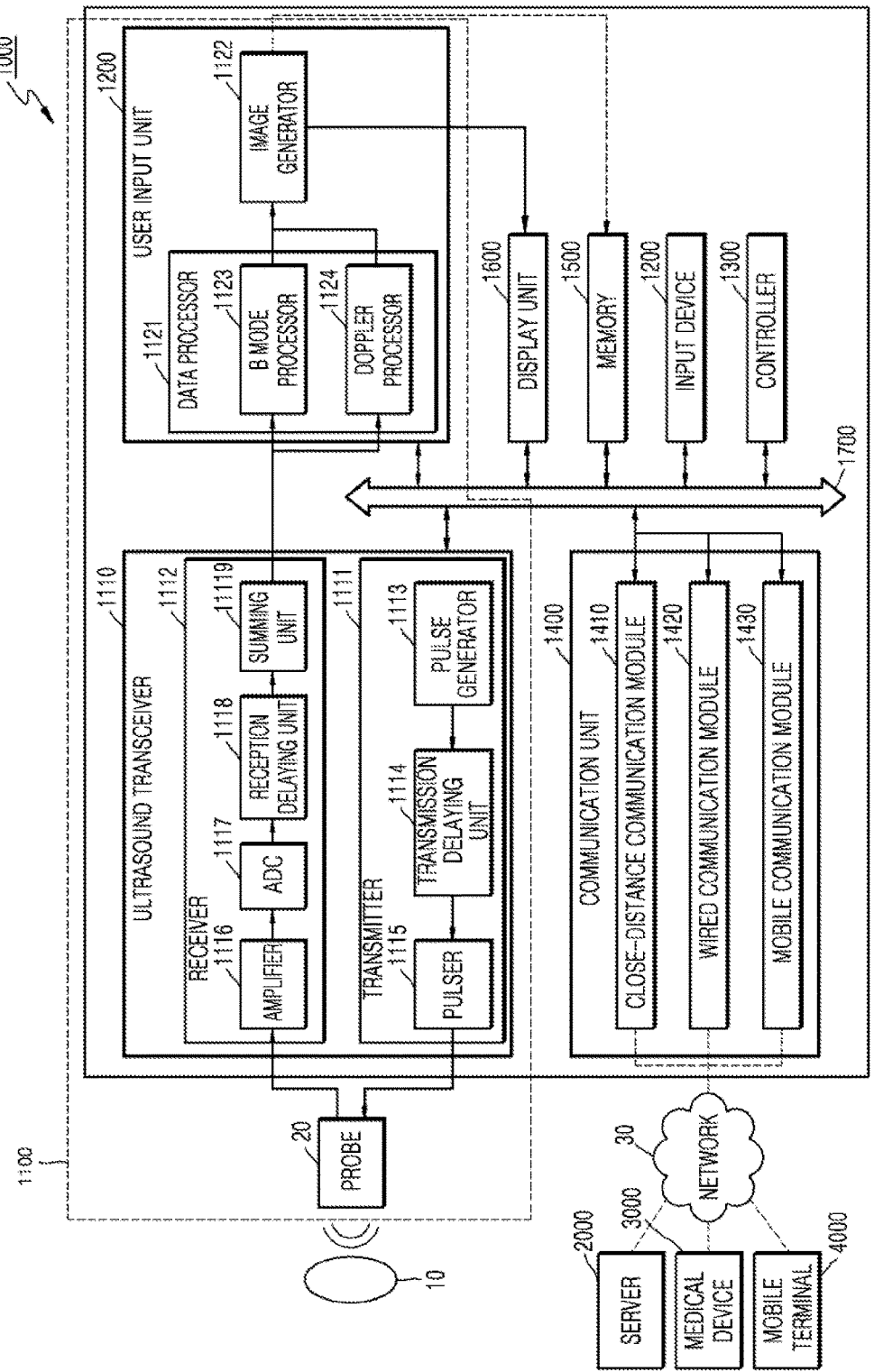
FIG. 12 is a block diagram of an ultrasound diagnosis apparatus to which an ultrasound system according to an embodiment may be applied.

FIG. 12 is a block diagram of an ultrasound diagnosis apparatus 10000 to which the ultrasound system 200 according to an embodiment may be applied. Referring to FIG. 12, the ultrasound diagnosis apparatus 10000 may include a probe 20, an ultrasound transceiver 1110, an image processor 1120, a communicator 1400, a display 1600, a memory 1500, an input device 1200, and a controller 1300, which may be connected to one another via buses 1700.

A method of editing an ultrasound image, according to an embodiment, may be performed by the ultrasound diagnosis apparatus 10000 of FIG. 12, and the ultrasound system 200 according to an embodiment may be included in the ultrasound diagnosis apparatus 10000 of FIG. 12.

The ultrasound system 200 of FIG. 2 may perform some or all functions performed by the ultrasound diagnosis apparatus 10000 of FIG. 12. The display 230 of FIG. 2 may correspond to the display 1600 of FIG. 12, the user interface 220 of FIG. 2 may correspond to a user input device 1200 of FIG. 12, and the controller 210 of FIG. 2 may include some or perform some functions of the ultrasound transceiver 1110, the image processor 1120, the communicator 1400, and the controller 1300 of FIG. 12.

The components of the ultrasound diagnosis apparatus 10000 of FIG. 12 will be described below.

An ultrasound image data acquiring unit 1100 according to an embodiment may obtain ultrasound image data of an object 10. The ultrasound image data according to an embodiment may be 2D ultrasound image data or 3D ultrasound image data of the object 10.

According to an embodiment, the ultrasound image data acquiring unit 1100 may include the probe 20, the ultrasound transceiver 1110, and the image processor 1120.

The probe 20 transmits ultrasound signals to the object 10 according to a driving signal applied by the ultrasound transceiver 1110 and receives ultrasound echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 10000 by wire or wirelessly. According to the embodiments of the present inventive concept, the ultrasound diagnosis apparatus 10000 may include a plurality of probes 20. According to an embodiment, the probe 20 may include at least one selected from a 1-dimensional (1 D) probe, a 1.5-dimenstional probe, a 2D (matrix) probe, and a 3D probe.

A transmitter 1111 supplies a driving signal to the probe 20. The transmitter 1111 includes a pulse generator 1113, a transmission delaying unit 1114, and a pulser 1115. The pulse generator 1113 generates pulses for forming transmission ultrasound waves based on a predetermined pulse repetition frequency (PRF), and the transmission delaying unit 1114 delays the pulses by delay times necessary for determining transmission directionality. The pulses, which have been delayed, correspond to a plurality of piezoelectric vibrators included in the probe 20, respectively. The pulser 1115 applies a driving signal (or a driving pulse) to the probe 20 based on timing corresponding to each of the pulses, which have been delayed.

A receiver 1112 generates ultrasound data by processing echo signals received from the probe 20. The receiver 1112 may include an amplifier 1116, an analog-to-digital converter (ADC) 1117, a reception delaying unit 1118, and a summing unit 1119. The amplifier 1116 amplifies echo signals in each channel, and the ADC 1117 performs analog-to-digital conversion on the each of the amplified signals. The reception delaying unit 1118 delays digital echo signals output by the ADC 1117 by delay times necessary for determining reception directionality, and the summing unit 1119 generates ultrasound data by summing the echo signals processed by the reception delaying unit 1118. For example, the summing unit 1119 may generate shoulder ultrasound image data. Alternatively, the summing unit 1119 may obtain shoulder ultrasound image data in real-time while a drug is injected into a bursa through a needle.

The image processor 1120 generates an ultrasound image by scan-converting ultrasound image data generated by the ultrasound transceiver 1110. The ultrasound image may be not only a grayscale ultrasound image obtained by scanning an object in an amplitude (A) mode, a brightness (B) mode, and a motion (M) mode, but also a Doppler image showing movements of an object via a Doppler effect. The Doppler image may be a blood flow Doppler image showing flow of blood (also referred to as a color Doppler image), a tissue Doppler image showing movements of tissue, or a spectral Doppler image showing a moving speed of an object as a waveform.

A B mode processor 1123 extracts B mode components from ultrasound image data and processes the B mode components. An image generator 1122 may generate a B mode image indicating signal intensities as brightness based on the B mode components extracted by the B mode processor 1123. For example, the image generator 1122 may generate a shoulder ultrasound image, including a deltoid, fat layers, bursae, and tendons, as a 2D B mode image.

The image generator 1122 may sequentially generate a plurality of B mode images. For example, the image generator 1122 may generate a first B mode image and a second B mode image. Alternatively, the image generator 1122 may generate a shoulder ultrasound image in real-time while a drug is injected into a bursa through a needle.

A Doppler processor 1124 may extract Doppler components from ultrasound image data, and the image generator 1122 may generate a Doppler image indicating movements of an object as colors or waveforms based on the extracted Doppler components.

According to an embodiment, the image generator 1122 may generate a 3D ultrasound image via volume-rendering with respect to volume data and may also generate an elasticity image by imaging the deformation of the object 10 due to pressure. Furthermore, the image generator 1122 may generate a speckle detection image by estimating moving paths of speckles from the ultrasound image data and indicating movements of the speckles as arrows or colors based on the estimated moving paths.

Furthermore, the image generator 1122 may display various pieces of additional information on an ultrasound image by using text and graphics. For example, the image generator 1122 may add at least one annotation related to all or some portions of the ultrasound image to the ultrasound image. That is, the image generator 1122 may analyze the ultrasound image and recommend at least one annotation related to all or some portions of the ultrasound image based on the analysis result. Alternatively, the image generator 1122 may add at least one annotation selected by the user to the ultrasound image.

The image processor 1120 may extract an interest region from the ultrasound image by using an image processing algorithm. In this case, the image processor 1120 may add colors, patterns, or boundaries to the interest region.

The user input device 1200 is a means via which a user (for example, a sonographer) inputs data for controlling the ultrasound diagnosis apparatus 10000. For example, the user input device 1200 may include a keypad, a dome switch, a touchpad (a capacitive overlay type, a resistive overlay type, an infrared beam type, an integral strain gauge type, a surface acoustic wave type, a piezoelectric type, etc.), a trackball, and a jog switch. However, embodiments of the present inventive concept are not limited thereto, and the user input device 1200 may further include any one of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

According to an embodiment, the user input device 1200 may detect not only a real-touch but also a proximity touch. The user input device 1200 may detect a touch input (for example, touch and holding, tapping, double tapping, or flicking) on an ultrasound image. Also, the user input device 1200 may detect a drag input from a point where a touch input is detected. The user input device 1200 may detect a multi-touch input (for example, pinching) on at least two points in the ultrasound image.

According to an embodiment, the user input device 1200 may receive an input for selecting an interest region in a B mode image. For example, the user input device 1200 may receive a user input for selecting an interest region, including a deltoid and tendons, in a shoulder ultrasound image.

The controller 1300 may control all operations of the ultrasound diagnosis apparatus 10000. For example, the controller 1300 may control operations of the ultrasound image data acquiring unit 1100, the user input device 1200, the communicator 1400, a memory 1500, and the display 1600.

The controller 1300 may detect a fat layer located between a deltoid and tendons based on echo signal intensity information included in shoulder ultrasound image data.

For example, the controller 1300 may detect a region of which intensities of echo signals are greater than a threshold value as a fat layer. Also, in the shoulder ultrasound image, the controller 1300 may determine a first boundary of which an intensity changing degree of echo signals is greater than a positive first threshold value as an upper portion of the fat layer and a second boundary of which an intensity changing degree of echo signals is less than a negative second threshold value as a lower portion of the fat layer. Also, the controller 1300 may detect a thickness of the fat layer based on a distance between the first and second boundaries.

The controller 1300 may detect a bursa located between the fat layer and the tendons by using a location of the fat layer. For example, the controller 1300 may determine an anechoic zone under the fat layer as the bursa.

Also, in the shoulder ultrasound image, the controller 1300 may extract a third boundary of which an intensity changing degree of echo signals is less than the first threshold value but greater than a third threshold value, and determine the third boundary as an upper portion of the tendons. In addition, the controller 1300 may detect a thickness of the bursa based on a distance between the second and third boundaries.

When an interest region is selected, the controller 1300 may detect the fat layer based on echo signal intensity information of the interest region. Also, the controller 1300 may change a location or a size of the interest region based on a location of the fat layer or a location of the bursa.

The communicator 1400 may include at least one component for allowing communication between the ultrasound diagnosis apparatus 10000 and a server 2000, the ultrasound diagnosis apparatus 10000 and a medical device 3000, and the ultrasound diagnosis apparatus 10000 and a mobile terminal 4000. For example, the communicator 1400 may include a close-distance communication module 1410, a wired communication module 1420, and a mobile communication module 1430.

The close-distance communication module 1410 refers to a module for close-distance communication within a predetermined distance. Examples of close-distance communication technologies may include Wi-Fi, Bluetooth, Bluetooth low energy (BLE), ultra wideband (UWB), ZigBee, near field communication (NFC), Wi-Fi Direct (WFD), and infrared data association (IrDA).

The wired communication module 1420 refers to a module for communication using electric signals or optical signals. Examples of wired communication technologies according to an embodiment may include communication via a pair cable, a coaxial cable, an optical fiber cable, and an Ethernet cable.

The mobile communication module 1430 transmits or receives wireless signals to at least one selected from a base station, an external device (3000, 4000), or the server 2000 on a mobile communication network. The wireless signals may be voice call signals, video call signals, or various types of data for transmission and reception of text/multimedia messages.

The communicator 1400 may be connected to a network 30 by wire or wirelessly to communicate with an external device (for example, the medical device 3000 or the mobile terminal 4000) or the server 2000. The communicator 1400 may exchange data with a hospital server or another medical apparatus in a hospital, which is connected thereto via a picture archiving and communication system (PACS). Furthermore, the communicator 1400 may perform data communication according to the digital imaging and communications in medicine (DICOM) standard.

The communicator 1400 may transmit or receive data related to diagnosis of the object 10, e.g., an ultrasound image, ultrasound image data, and Doppler data of the object 10, via the network 30 and may also transmit or receive medical images captured by another medical apparatus, e.g., a computed tomography (CT) apparatus, a magnetic resonance imaging (MRI) apparatus, or an X-ray apparatus. Furthermore, the communicator 1400 may receive information about a diagnosis history or medical treatment schedule of a patient from the server 2000 and utilize the received information for the diagnosis of the object 10.

The memory 1500 may store a program for processing the controller 1300 or data that is input or output (for example, ultrasound image data, information about a drug spreading boundary, information of a subject to be tested, probe information, or a body marker).

The memory 1500 may include at least one type of storage medium selected from a flash memory, a hard disk drive, a multimedia card micro type memory, a card type memory (for example, a secure digital (SD) or an XD memory), random access memory (RAM), static RAM (SRAM), read-only memory (ROM), electrically erasable programmable ROM (EEPROM), programmable ROM (PROM), a magnetic memory, a magnetic disc, and an optical disc. Also, the ultrasound diagnosis apparatus 10000 may manage a web storage or a cloud server that performs as a storage like the memory 1500 on the Internet.

The display 1600 displays information processed by the ultrasound diagnosis apparatus 10000. For example, the display 1600 may display an ultrasound image or a user interface (UI) or a graphical UI (GUI) related to a control panel.

According to an embodiment, the display 1600 may display location information of a bursa on a shoulder ultrasound image generated based on shoulder ultrasound image data. For example, the display 1600 may display a preset indicator at a location of the bursa on the shoulder ultrasound image. The display 1600 may display a first boundary line that distinguishes the bursa from a fat layer and a second boundary line that distinguishes the bursa from tendons.

When the display 1600 and a touch pad are layered and thus provided as a touch screen, the display 1600 may be used as not only an output device but also as an input device. The display 1600 may include at least one selected from a liquid crystal display (LCD), a thin film transistor LCD, an organic light-emitting diode display, a flexible display, a 3D display, and an electrophoretic display. Also, according to the embodiments of the present inventive concept, the number of display units 1600 included in the ultrasound diagnosis apparatus 10000 may be two or more.

A method according to exemplary embodiments may be implemented through program instructions that are executable via various computer devices and recorded in computer-readable recording media. The computer-readable recording media may include program instructions, data files, data structures, or a combination thereof. The program instructions may be specifically designed for the present inventive concept or well-known to one of ordinary skill in the art of computer software. Examples of the computer-readable recording media include magnetic media (e.g., hard disks, floppy disks, or magnetic tapes), optical media (e.g., CD-ROMs or DVDs), magneto-optical media (e.g., floptical disks), and hardware devices specifically designed to store and execute the program instructions (e.g., ROM or RAM). Examples of the program instructions not only include machine codes that are made by compilers but also computer-executable high level language codes that may be executed by using an interpreter.

As described above, according to the one or more of the above exemplary embodiments, labels may be more accurately and conveniently edited with regard to geometric shapes of labels generated on a 3D ultrasound image.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound system comprising:
a display displaying an ultrasound image generated based on ultrasound volume data obtained from an object and a plurality of labels generated based on the ultrasound volume data and a predetermined threshold value;
a user interface receiving a selection signal for selecting at least one label from the plurality of labels and an adjustment signal for adjusting the predetermined threshold value; and
a controller generating at least one new label based on a threshold value adjusted according to the adjustment signal,
wherein the display replaces and displays the at least one new label on a region corresponding to the at least one selected label,
wherein when the display replaces and displays the at least one new label on the region corresponding to the at least one selected label, at least one label that is not selected according to the selection signal from among the plurality of labels generated based on the predetermined threshold value is displayed as it is,
wherein the selection signal is for inputting a line crossing at least two labels selected from the plurality of labels.

2. The ultrasound system of claim 1, wherein the ultrasound volume data comprises a plurality of voxels, and
the selection signal is for selecting coordinate information corresponding to at least one voxel comprised in the at least one selected label.

3. The ultrasound system of claim 1, wherein the selection signal is for inputting coordinate information in regions corresponding to the at least two labels.

4. The ultrasound system of claim 1, wherein when a first label is selected from the plurality of labels according to the selection signal, the display displays a second label on a region corresponding to the first label based on the adjusted threshold value, and
the second label is larger or smaller than the first label.

5. The ultrasound system of claim 4, wherein when the ultrasound volume data comprises a plurality of voxels and the plurality of labels comprise a first label, a number of voxels comprised in the first label according to the predetermined threshold value is different from a number of voxels comprised in the second label according to the adjusted threshold value.

6. The ultrasound system of claim 1, wherein when a first label is selected from the plurality of labels according to the selection signal, the display separately displays at least two labels based on the adjusted threshold value on a region corresponding to the first label.

7. The ultrasound system of claim 1, wherein when a first label is selected from the plurality of labels according to the selection signal and a threshold value used to generate the at least one new label is gradually changed from the predetermined threshold value to the adjusted threshold value according to the adjustment signal, a label displayed on a region corresponding to the first label is gradually reduced in size and then split into at least two labels.

8. The ultrasound system of claim 1, wherein when a first label and a second label are selected from the plurality of labels according to the selection signal, the display displays a third label, which indicates that the first and second labels are merged based on the adjusted threshold value, on a combined region corresponding to the first and second labels.

9. The ultrasound system of claim 1, wherein when a first label and a second label are selected from the plurality of labels according to the selection signal and a threshold value used to generate the at least one new label is gradually changed from the predetermined threshold value to the adjusted threshold value according to the adjustment signal, a label displayed on a region corresponding to the first label and a label displayed on a region corresponding to the second label are respectively gradually increased in size and merged into a third label.

10. The ultrasound system of claim 1, wherein the ultrasound volume data comprises a plurality of voxels, and
when the user interface receives a selection input for selecting coordinates corresponding to a voxel not comprised in the plurality of labels according to the selection signal, the display displays at least one new label generated based on the adjusted threshold value on a region comprising the coordinates.

11. The ultrasound system of claim 1, wherein when a first label is selected from the plurality of labels, the display does not display any labels based on the adjusted threshold value on a region corresponding to the first label.

12. The ultrasound system of claim 1, wherein when a first label is selected from the plurality of labels according to the selection signal and a threshold value used to generate the at least one new label is gradually changed from the predetermined threshold value to the adjusted threshold value according to the adjustment signal, a label displayed on a region corresponding to the first label is gradually reduced in size and deleted.

13. A method of displaying a label in an ultrasound system, the method comprising:
displaying an ultrasound image generated based on ultrasound volume data obtained from an object and a plurality of labels generated based on the ultrasound volume data and a predetermined threshold value;
receiving a selection signal for selecting at least one label from the plurality of labels;
receiving an adjustment signal for adjusting the predetermined threshold value;
generating at least one new label based on a threshold value adjusted according to the adjustment signal; and
replacing and displaying the at least one new label on a region corresponding to the at least one selected label,
wherein the replacing comprises displaying at least one label that is not selected according to the selection signal from among the plurality of labels generated based on the predetermined threshold value as it is,
wherein the selection signal is for inputting a line crossing at least two labels selected from the plurality of labels.

14. The method of claim 13, wherein the ultrasound volume data comprises a plurality of voxels, and
the selection signal is for selecting coordinate information corresponding to at least one voxel comprised in the at least one selected label.

15. The method of claim 13, wherein the selection signal is for inputting coordinate information in regions corresponding to the at least two labels.

16. The method of claim 13, wherein when a first label is selected from the plurality of labels according to the selection signal, a second label is displayed on a region corresponding to the first label based on the adjusted threshold value, and
the second label is larger or smaller than the first label.

17. The method of claim 13, wherein when the ultrasound volume data comprises a plurality of voxels and the plurality of labels comprises a first label and a second label, a number of voxels comprised in the first label according to the predetermined threshold value is different from a number of voxels comprised in the second label according to the adjusted threshold value.

18. The method of claim 13, wherein when a first label is selected from the plurality of labels according to the selection signal, at least two labels are separately displayed based on the adjusted threshold value on a region corresponding to the first label.

19. The method of claim 13, wherein when a first label is selected from the plurality of labels according to the selection signal and a threshold value used to generate the at least one new label is gradually changed from the predetermined threshold value to the adjusted threshold value according to the adjustment signal, a label displayed on a region corresponding to the first label is gradually reduced in size and then split into at least two labels.

20. The method of claim 13, wherein when a first label and a second label are selected from the plurality of labels according to the selection signal, a third label is displayed, which indicates that the first and second labels are merged based on the adjusted threshold value, on a combined region corresponding to the first and second labels.

21. The method of claim 13, wherein when a first label and a second label are selected from the plurality of labels according to the selection signal and a threshold value used to generate the at least one new label is gradually converted from the predetermined threshold value to the adjusted threshold value according to the adjustment signal, a label displayed on a region corresponding to the first label and a label displayed on a region corresponding to the second label are respectively gradually increased in size and merged into a third label.

22. The method of claim 13, wherein the ultrasound volume data comprises a plurality of voxels, and
when a selection input for selecting coordinates corresponding to a voxel not comprised in the plurality of labels according to the selection signal is displayed, at least one new label generated based on the adjusted threshold value is displayed on a region comprising the coordinates.

23. The method of claim 13, wherein when a first label is selected from a plurality of labels, no label is displayed based on the adjusted threshold value on a region corresponding to the first label.

24. The method of claim 13, wherein when a first label is selected from the plurality of labels according to the selection signal and a threshold value used to generate the at least one new label is gradually converted from the predetermined threshold value to the adjusted threshold value according to the adjustment signal, a label displayed on a region corresponding to the first label is gradually reduced in size and deleted.

25. A non-transitory computer-readable recording medium having recorded thereon a program, which, when executed by a computer, performs the method of claim 13.

* * * * *